(12) United States Patent
Kaneko et al.

(10) Patent No.: US 9,798,044 B2
(45) Date of Patent: Oct. 24, 2017

(54) NONLINEAR OPTICAL MATERIALS AND NONLINEAR OPTICAL DEVICE USING THE SAME

(71) Applicant: FUJIFILM Corporation, Tokyo (JP)

(72) Inventors: Akihiro Kaneko, Kanagawa (JP); Masaaki Tsukase, Kanagawa (JP); Masataka Satou, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 440 days.

(21) Appl. No.: 14/497,593

(22) Filed: Sep. 26, 2014

(65) Prior Publication Data

US 2015/0014607 A1    Jan. 15, 2015

Related U.S. Application Data

(63) Continuation of application No. PCT/JP2013/059102, filed on Mar. 27, 2013.

(30) Foreign Application Priority Data

Mar. 29, 2012  (JP) .................. 2012-078096

(51) Int. Cl.
| | |
|---|---|
| C09K 9/00 | (2006.01) |
| G02B 1/08 | (2006.01) |
| C07D 409/04 | (2006.01) |
| C07D 417/06 | (2006.01) |
| C07D 495/04 | (2006.01) |
| C07D 207/44 | (2006.01) |
| G02F 1/361 | (2006.01) |
| C07D 417/14 | (2006.01) |
| G02B 5/30 | (2006.01) |

(52) U.S. Cl.
CPC ............ *G02B 1/08* (2013.01); *C07D 207/44* (2013.01); *C07D 409/04* (2013.01); *C07D 417/06* (2013.01); *C07D 417/14* (2013.01); *C07D 495/04* (2013.01); *G02B 5/3025* (2013.01); *G02F 1/3612* (2013.01); *G02F 1/3614* (2013.01); *G02F 1/3615* (2013.01)

(58) Field of Classification Search
USPC .................. 252/583; 548/550, 526, 194, 527
See application file for complete search history.

(56) References Cited

U.S. PATENT DOCUMENTS

| | | | |
|---|---|---|---|
| 3,013,013 A | 12/1961 | Carboni | |
| 6,361,717 B1 | 3/2002 | Dalton et al. | |
| 7,307,173 B1* | 12/2007 | Jen ..................... | C07D 207/456 548/202 |
| 7,888,387 B2 | 2/2011 | Huang et al. | |
| 2009/0223627 A1 | 9/2009 | Choi et al. | |

FOREIGN PATENT DOCUMENTS

| | | |
|---|---|---|
| JP | 06-202177 A | 7/1994 |
| JP | 2007-57941 A | 3/2007 |

OTHER PUBLICATIONS

Search Report dated Jul. 2, 2013 issued by the International Searching Authority in counterpart International Patent Application No. PCT/JP2013/059102 (PCT/ISA/210).
Written Opinion dated Jul. 2, 2013 issued by the International Searching Authority in counterpart International Patent Application No. PCT/JP2013/059102 (PCT/ISA/237).
A. Leclercq et al.; "Quantum-chemical investigation of second-order nonlinear optical chromophores: Comparison of strong nitrile-based acceptor end groups and role of auxiliary donors and acceptors"; The Journal of Chemical Physics; vol. 124; No. 4; Dec. 8, 2006; 8 pages; DOI: 10.1063/1.2155385.
Donald M. Burland et al.; "Second-Order Nonlinearity in Poled-Polymer Systems"; Chemical Reviews; vol. 94; No. 1; 1994; pp. 31-75.
"A Study on the Synthesis of Side-chain Nonlinear Optical Polymer with a Strong Acceptor"; a doctoral thesis of Tohoku University; 2006; 7 pages.
Min Ju Cho et al.; "A tricyanopyrroline-based nonlinear optical chromophore bearing a lateral moiety: A novel steric technique for enhancing the electro-optic effect"; Dyes and Pigments; ScienceDirect; vol. 79; No. 2; Nov. 2008; 8 pages.
Cheng Zhang et al.; "Low $V_\pi$ Electrooptic Modulators from CLD-1: Chromophore Design and Synthesis, Material Processing, and Characterization"; Chem. Mater.; vol. 13; No. 9; 2001; pp. 3043-3050.

* cited by examiner

*Primary Examiner* — Monique Peets
(74) *Attorney, Agent, or Firm* — Sughrue Mion, PLLC

(57) ABSTRACT

There is provided an organic nonlinear optical material including a polymer binder and a compound represented by the following Formula (I):

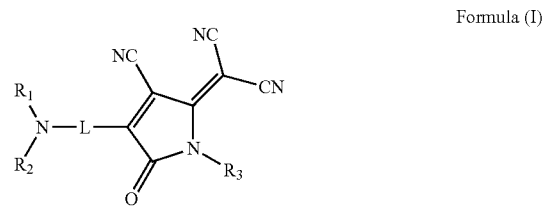

Formula (I)

wherein, in Formula (I),
$R_1$ and $R_2$ each independently represent a substituted or unsubstituted alkyl group or a substituted or unsubstituted aryl group;
$R_3$ represents a hydrogen atom, a substituted or unsubstituted alkyl group, or a substituted or unsubstituted aryl group; and
L represents a divalent linking group connecting a nitrogen atom and an oxopyrroline ring having a dicyanomethylidene group in a π-conjugated system containing an azo group (—N=N—).

1 Claim, No Drawings

NONLINEAR OPTICAL MATERIALS AND NONLINEAR OPTICAL DEVICE USING THE SAME

CROSS REFERENCE TO RELATED APPLICATION

This is a continuation of International Application No. PCT/JP2013/059102 filed on Mar. 27, 2013, and claims priority from Japanese Patent Application No. 2012-078096 filed on Mar. 29, 2012, the entire disclosures of which are incorporated herein by reference.

TECHNICAL FIELD

The present invention relates an organic nonlinear optical material which is suitably used for an organic nonlinear optical device that is useful in the field of optoelectronics and photonics, which may be applied to optical modulators, optical switches, optical integrated circuits, optical computers, an optical memory, a wavelength conversion device, a hologram device or the like, which are useful in the field of optical information communication, optical information processing, imaging, using light.

BACKGROUND ART

With the progress of advanced information society, numerous attempts to use optical technology with respect to the transmission, processing, and recording of information have been made. In such a situation, a material (a nonlinear optical material) exhibiting a nonlinear optical effect has been noted in the field of optoelectronics and photonics. The nonlinear optical effect is a phenomenon showing the non-linear relationship between the electric field applied and the electrical polarization resulting from when the strong electric field (light field) is applied to a material, and a nonlinear optical material refers to a material that exhibits significantly such nonlinearity. As a nonlinear optical material using a secondary nonlinear response, a material which generates a second harmonic wave, a material that exhibits Pockels effect (primary electro-optic effect) causing refractive index changes in proportion to the primary of an electric field or the like are known. Especially, the application of the latter has been investigated as an electro-optic (EO) light modulation device or a photorefractive device. Further, it is expected to exhibit a piezoelectric and pyroelectric property, and also its application to various fields.

As a secondary nonlinear optical material, an inorganic nonlinear optical material such as lithium niobate or potassium dihydrogen phosphate has already been put into practical use and has been widely used, but recently an organic material which 1) represents a large nonlinearity,
2) has a fast response rate,
3) has a high optical damage threshold,
4) is possible to design a great variety of molecules, and
5) is excellent in manufacturing aptitude, etc. has been noted and thus its vigorous research and development toward the practical use has been made.

However, for the expression of the secondary nonlinear optical effect, since it is necessary that the polarization induced by an electric field lacks inversion symmetry center and the nonlinear optical response group or molecule showing a nonlinear optical effect needs to be placed in a structure which lacks inversion symmetry, the organic compound having a nonlinear optical activity is roughly divided into a system (hereinafter referred to as "crystal system") which was crystallized in the crystal structure which lacks symmetrical center and a system (hereinafter referred to as "polymeric system") whose organic compound having a nonlinear optical activity was oriented by any means by dispersing or binding the corresponding organic compound having a nonlinear optical activity to the polymer binder.

It is known that the organic nonlinear optical material of the crystal system may exhibit very high nonlinear optical performance, but there are problems in that the production of large organic crystals necessary for devices is difficult, and the strength of the organic crystal is very brittle and damaged in the process of devices. In contrast, the organic nonlinear optical material of the polymeric system gives desirable properties such as useful film-forming properties, the mechanical strength when a device is produced by the polymer binder, and its potential for practical use becomes high and promising.

In order to place the nonlinear optical response group or molecule showing a nonlinear optical effect as in the structure which lacks inversion symmetry center as conventional techniques in the organic nonlinear optical material of the polymeric system, it is possible to introduce a nonlinear optical response group or molecule showing a nonlinear optical effect in the polymeric binder. For example, it has been widely used to orient the dipoles by an electric field. The orientation control by the electric field is referred to as "poling", and the poled organic polymer is referred to as "an electric field oriented polymer (poled polymer)". That is, this is a technique to align the dipole of the response group or molecule showing the secondary nonlinear optical effect by applying a high voltage at a temperature higher than the glass transition temperature of the base polymer, and then to freeze the orientation of the dipole by the electric field by cooling. For example, an electro-optical (EO) light modulator made in accordance with the present method is known However, there is a problem that the dipole of the response group or molecule showing the secondary nonlinear optical effect oriented by poling causes the thermal relaxation of orientation over time, and concomitantly the nonlinear optical properties of a material become deteriorated.

Thus, for the organic nonlinear optical material of polymeric system, it is required to include an organic compound having high nonlinear optical activity and a polymer binder being capable of keeping the orientation state of the organic compound having implied nonlinear optical activity stable in addition to having high film forming properties, mechanical strength, and the like.

As for the organic compounds having the above mentioned nonlinear optical active, tertiary amine derivatives such as Disperse Red 1 (generally, abbreviated as DR1) or 4-(Dicyanomethylene)-2-methyl-6-(4-dimethylaminostyryl)-4H-pyran (generally, abbreviated as DCM) are well known.

However, the organic compound itself does not have large nonlinear optical characteristics, and thus further improvement has been desired.

To solve this problem, the search for an organic compound having large nonlinear optical property has been actively carried out, and the effectiveness of an organic compound having tricyanofuran structure having a high electron-withdrawing property or an organic compound having a long π-conjugated bond group has been reported, but it is known that the organic compounds are decomposed and they do not withstand a practical use as an optical device in continuous driving in light wavelength (for example, 1.33

μm) that is intended to be actual driving (for example, see Patent Documents 1 and 2 and Non-patent Document 1).

Further, an organic compound having a tricyanopyrroline structure as a high electron-withdrawing group or an organic compound having a tricyanopyrroline structure and a long π-conjugated bond group has also been reported (for example, Patent Document 3 and 4), but light resistance was still insufficient. In addition, in the Non-patent Document 2, an organic compound having a tricyanopyrroline structure was disclosed, but it was described that the synthesis was not possible.

Meanwhile, as the polymeric binder, polymethylmethacrylate (in general, abbreviated as PMMA) has been studied most frequently, but the glass transition temperature of PMMA is as low as 100° C., and the orientation state of an organic nonlinear optical material of a polymeric system using PMMA a polymer binder is relaxed slowly even at room temperature, and the nonlinear optical performance becomes significantly deteriorated over time. Thus, it is known that PMMA may not withstand the practical use as a functional device (for example, see Non-patent Document 3).

To solve this problem, the search for the polymer binder instead of PMMA has been actively carried out, and the effectiveness of the polymer having higher glass transition temperature than that of PMMA such as polycarbonate, polyimide, polysulfone or the like has been reported (for example, see Patent Document 5), but there was a problem that in the case of using a polymer binder having this high glass transition temperature, the temperature of the heating required for the electric field poling will rise, or in the case of using the DR1 or DCM as an organic compound having a nonlinear optical activity, this low molecular compound was vanished or oxidized by sublimation.

In addition, in consideration of the solder mounting such as a printed circuit, it becomes exposed to the heating conditions of 230° C. or more even in a short time, and the problem such as sublimation or decomposition of low molecular compound becomes more remarkable.

Further, since the organic compound is exposed to harsh conditions that still higher electric field is applied to the heating at a high temperature during poling, it may be stable only by heating. But, there is not less cases that the compound will decompose under the conditions of heating or high electric field. However, it is difficult to clarify the molecular design that confers voltage stability to the organic compounds having a nonlinear optical activity, there is also little discussed with respect to voltage resistance and a tendency that large nonlinear optical activity is priority in molecular design of the same compound is strong. Therefore, in order to obtain a high orientation state without damaging the nonlinear optical activity of the material, it is not possible to search the poling condition such as temperature, electric field, time, and the like in turns. However, there has been a demand for a compound being fundamentally stable about poling conditions without a guarantee that there is no essential solution and suitable conditions are found.

CITATION LIST

Patent Documents

[Patent Document 1] U.S. Pat. No. 6,361,717
[Patent Document 2] U.S. Pat. No. 7,888,387
[Patent Document 3] U.S. Pat. No. 3,013,013
[Patent Document 4] U.S. Pat. No. 7,307,173
[Patent Document 5] Japanese Patent Application Laid-Open No. Hei 6-202177

Non-Patent Documents

[Non-patent Document 1] Chemistry of Materials (2001), Vol. 13, pp. 3043-3050
[Non-patent Document 2] "A Study on the Synthesis of Side-chain Nonlinear Optical Polymer with a Strong Acceptor," a doctoral thesis of Tohoku University (2006)
[Non-patent Document 3] Chemical Reviews (1994), Vol. 94, No. 1, pp. 31-75

SUMMARY OF THE INVENTION

Problems to be Solved

The present invention aims to solve the problems of the prior art described above.

That is, an object of the present invention is to provide an organic nonlinear optical material having an excellent nonlinear optical performance and a good stability and a nonlinear optical device using the same, which may use effectively a polymeric binder having a high glass transition temperature by using an organic compound having excellent specific nonlinear optical activities being excellent in nonlinear optical performance, light resistance, oxidation resistance, sublimation resistance or the like.

Means for Solving the Problems

The present inventors found that the compounds represented by the following Formulas (I) to (V) containing a substituted amino group as an electron-donating group, tricyanopyrroline structure as an electron-withdrawing group, and an azo group in the π-conjugated chain has nonlinear optical activity and also light resistance, sublimation resistance, heat resistance during repeating the synthesis and the evaluation to solve the above mentioned problems.

Furthermore, surprisingly, the compound represented by the following Formulas (I) to (V) has an excellent stability during the electric field poling. It was unimaginable that the compound of the present invention may withstand severe conditions of high temperature and high electric field. Since this compound may conduct electric field poling without deterioration of the dye by dispersing or binding a binder polymer having high glass transition temperature, it is possible to maintain an excellent nonlinear optical property stably for a long time. Therefore, it was found that the organic nonlinear optical material of the present invention may solve the above mentioned problems to complete the present invention.

[1] An organic nonlinear optical material including a polymer binder and a compound represented by the following Formula (I).

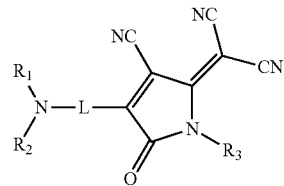

Formula (I)

(In Formula (I), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

L connects a nitrogen atom and an oxopyrroline ring having a dicyanomethylidene group in π-conjugated system, and L represents a divalent linking group containing an azo group (—N=N—) in the π-conjugated system.)

[2] The organic nonlinear optical material described in the above [1], wherein Formula (I) is represented by the following Formula (II).

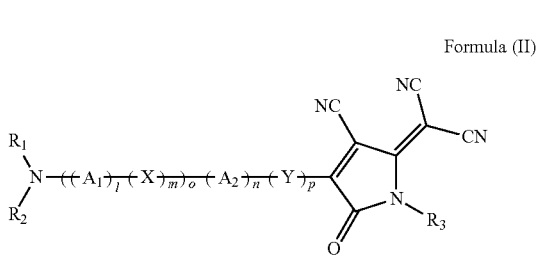

Formula (II)

(In Formula (II), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$A_1$ and $A_2$ each independently represent a substituted or unsubstituted aromatic group.

X represents —$CR_4$=$CR_5$—, —C≡C—, —$CR_6$=N—, —N=$CR_7$—, or —N=N—.

Y represents —$CR_8$=$CR_9$—, or a substituted or unsubstituted aromatic group.

$R_4$, $R_5$, $R_6$, $R_7$, $R_8$ and $R_9$ each independently represent a hydrogen atom, a substituted or unsubstituted alkyl group, or a substituted or unsubstituted aryl group.

l and n each independently represent an integer of 0 to 3.

m, o, and p each independently represent an integer of 1 to 3.

Each $R_4$, $R_5$, $R_6$, $R_7$, $R_8$, $R_9$, $A_1$, $A_2$, X, Y, l and m may be the same or different, and at least one of X contains —N=N—.)

[3] The organic nonlinear optical material described in the above [2], wherein n in Formula (II) represents an integer of 1 to 3.

[4] The organic nonlinear optical material described in the above [2] or [3], wherein Y in Formula (II) represents —$CR_8$=$CR_9$— or a substituted or unsubstituted thienylene group, and $R_8$ and $R_9$ each independently represent a hydrogen atom, a substituted or unsubstituted alkyl group, or a substituted or unsubstituted aryl group.

[5] The organic nonlinear optical material disclosed in any one of the above [2] to [4], wherein $A_1$ in Formula (II) represents a substituted aryl group or a 5- or 6-membered substituted heteroaryl group containing either an oxygen atom, a sulfur atom, or a nitrogen atom as a hetero atom.

[6] The organic nonlinear optical material disclosed in any one of the above [2] to [4], wherein in Formula (II) $A_1$ represents a substituted or unsubstituted phenylene group, X represents —N=N—, l and m represent 1, n and p represent an integer satisfying the relationship formula of 2≤n+p≤3, and $A_2$ represents any one of the below.

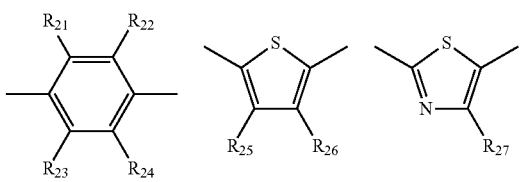

($R_{21}$, $R_{22}$, $R_{23}$ and $R_{24}$ each independently represent a hydrogen atom, a halogen atom, a cyano group, a substituted or unsubstituted alkyl group, or a substituted or unsubstituted aryl group, a substituted or unsubstituted heteroaryl group, a substituted or unsubstituted alkoxy group, a substituted acyl group, or a substituted or unsubstituted carbamoyl group, $R_{25}$ and $R_{26}$ each independently represent a hydrogen atom, a halogen atom, a cyano group, a substituted or unsubstituted alkyl group, or a substituted or unsubstituted aryl group, a substituted or unsubstituted heteroaryl group, a substituted or unsubstituted alkoxy group, or a substituted acyl group, $R_{27}$ represents a hydrogen atom, a halogen atom, a cyano group, a substituted or unsubstituted alkoxy group, a substituted or unsubstituted alkyl group, a substituted or unsubstituted aryl group, a substituted or unsubstituted heteroaryl group, or a substituted oxycarbonyl group, and each $R_{21}$, $R_{22}$, $R^{23}$, $R_{74}$, $R_{25}$, $R_{26}$ and $R_{27}$ may be the same or different, and $R_{21}$ and $R_{22}$, $R_{23}$ and $R_{24}$, or $R_{25}$ and $R_{26}$ may be linked to each other to form a ring.)

[7] The organic nonlinear optical material disclosed in any one of the above [2] to [4] and [6], wherein the following Formula (II) is represented by the following Formula (III).

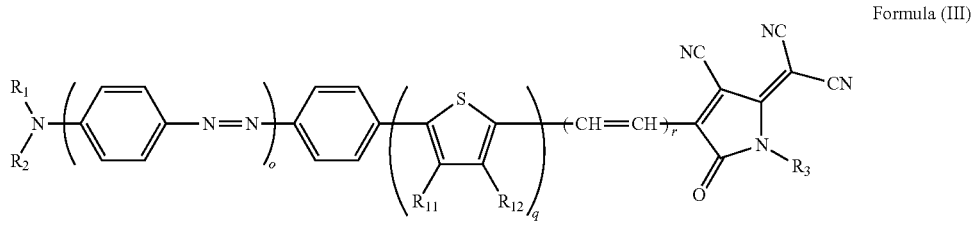

Formula (III)

(In Formula (III), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

o represents an integer of 1 to 3.

$R_{11}$ and $R_{12}$ each independently represent a hydrogen atom, a substituted or unsubstituted alkyl group or a substituted or unsubstituted alkoxy group. They may be linked to each other to form a ring.

q and r each independently represent an integer of 0 to 3. However, q and r will not be 0 at the same time.)

[8] The organic nonlinear optical material disclosed in any one of the above [2] to [6], wherein the following Formula (II) is represented by the following Formula (IV).

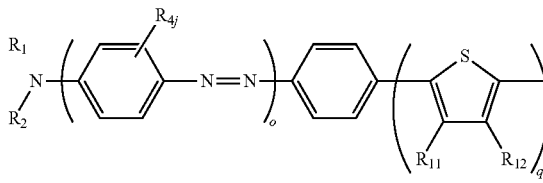
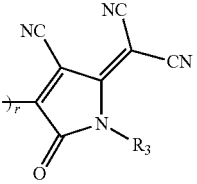

Formula (IV)

(In Formula (IV), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$R_{4j}$ represents a substituted or unsubstituted alkyl group, or a substituted or unsubstituted aryl group, a substituted or unsubstituted heteroaryl group, a substituted or unsubstituted alkoxy group, a substituted or unsubstituted alkylthio group, a substituted or unsubstituted carbamoyl group, or a substituted or unsubstituted acylamino group, $R_{4j}$ may be singular or plural, and each $R_{4j}$ may be the same or different.

o represents an integer of 1 to 3.

$R_{11}$ and $R_{12}$ each independently represent a hydrogen atom, a substituted or unsubstituted alkyl group or a substituted or unsubstituted alkoxy group. They may be linked to each other to form a ring.

q and r each independently represent an integer of 0 or 1. However, q and r will not be 0 at the same time.)

[9] The organic nonlinear optical material disclosed in any one of the above [2] to [4], wherein the following Formula (II) is represented by the following Formula (V).

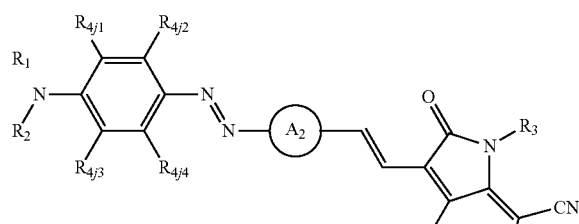

Formula (V)

(In Formula (V), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$R_{4j1}$ to $R_{4j4}$ each independently represent a hydrogen atom, a substituted or unsubstituted alkyl group, or a substituted or unsubstituted aryl group, a substituted or unsubstituted heteroaryl group, a substituted or unsubstituted alkoxy group, a substituted or unsubstituted alkylthio group, a substituted or unsubstituted carbamoyl group, or a substituted or unsubstituted acylamino group.

$A_2$ represents a substituted or unsubstituted aromatic group.)

[10] The organic nonlinear optical material disclosed in any one of the above [1] to [9], wherein the glass transition temperature of the polymeric binder is at least 130° C.

[11] The organic nonlinear optical material disclosed in any one of the above [1] to [10], wherein comprising 1% by mass to 90% by mass of the compound represented by Formula (I).

[12] An optical device obtained by using the organic nonlinear optical material disclosed in any one of the above [1] to [11].

[13] An optical modulation device obtained by using the organic nonlinear optical material disclosed in any one of the above [1] to [11].

[14] A compound represented by the following Formula (II).

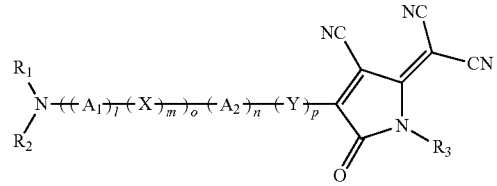

Formula (II)

(In Formula (II), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$A_1$ and $A_2$ each independently represent a substituted or unsubstituted aromatic group.

X represents —$CR_4$=$CR_5$—, —C≡C—, —$CR_6$=N—, —N=$CR_7$— or —N=N—.

Y represents —$CR_8$=$CR_9$— or a substituted or unsubstituted aromatic group.

$R_4$, $R_5$, $R_6$, $R_7$, $R_8$ and $R_9$ each independently represent a hydrogen atom, a substituted or unsubstituted alkyl group, or a substituted or unsubstituted aryl group.

l and n each independently represent an integer of 0 to 3.

m, o, and p each independently represent an integer of 1 to 3.

Each $R_4$, $R_5$, $R_6$, $R_7$, $R_8$, $R_9$, $A_1$, $A_2$, X, Y, l and m may be the same or different, and at least one of X contains —N=N—.)

Advantageous Effects of Invention

An organic nonlinear optical material of the present invention is characterized in that it includes a polymer binder and an organic compound having a specific nonlinear optical activity being excellent in a nonlinear optical performance, heat resistance, sublimation resistance, voltage resistance. Accordingly, a polymeric binder having a high stability of the light (e.g. wavelength of 1.3 µm) and a high nonlinear optical activity during the actual drive of heat or voltage in the process for achieving the oriented state, and also having a high glass transition temperature may be applied. Therefore, there appears a desirable effect that may maintain such an oriented state of the organic compound having a nonlinear optical activity for a long period of time.

A nonlinear optical device being excellent in the stability and various characteristics may be embodied by using the organic nonlinear optical material of the present invention

DETAILED DESCRIPTION FOR CARRYING OUT THE INVENTION

Hereinafter, the invention may be described on the basis of the exemplary embodiments of the present invention, but so long as it does not exceed the gist of the present invention, it is not intended to be limited only to the embodiments described.

Further, in this specification, the numerical range expressed by using "~" means a range including the lower and upper limits of numerical values described before and after "~".

An organic nonlinear optical material of the present invention includes a polymer binder and a compound represented by the following Formula (I).

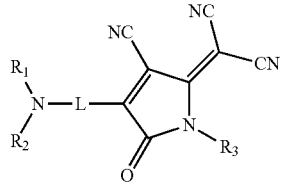

Formula (I)

(In Formula (I), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

L connects a nitrogen atom and an oxopyrroline ring having a dicyanomethylidene group in π-conjugated system, and L represents a divalent linking group containing an azo group (—N=N—) in the π-conjugated system.)

The oxopyrroline ring having dicyanomethylidene group as used herein represents the following partial structure. The asterisk represents the binding site of the L.

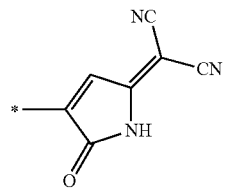

<Organic Compound Having a Nonlinear Optical Activity>

The organic nonlinear optical material of the present invention includes a compound represented by the above mentioned Formula (I) (hereinafter, referred also to a compound of Formula (I)) as an organic compound having a nonlinear optical activity. Here, the compound represented by Formula (I) may be dispersed in a molecular state or a microcrystalline state in a polymeric binder described later, or may be linked chemically in the main chain or side chains of the polymer binder. When dispersed in a polymeric binder, the compound may be preferably to be dispersed in a molecular state in terms of optical quality such as transparency.

In Formula (I), $R_1$ and $R_2$ each independently represent a substituted or unsubstituted alkyl group or a substituted or unsubstituted aryl group.

Examples of the alkyl group include a methyl group, an ethyl group, an n-propyl group, an i-propyl group, an n-butyl group, a t-butyl group, an n-hexyl group, a 2-ethylhexyl group, and a t-octyl group, preferably an ethyl group, an n-propyl group, an n-butyl group, an n-hexyl group, and a 2-ethylhexyl group, and more preferably an ethyl group, an n-butyl group, and an n-hexyl group.

Examples of the aryl group include a phenyl group and a naphthyl group, and preferably a phenyl group.

Examples of the substituent groups when $R_1$ and $R_2$ each represent a substituted alkyl group or a substituted aryl group include a halogen atom, an alkyl group, a cycloalkyl group, an alkenyl group, an aryl group, a heteroaryl group, a cyano group, a hydroxyl group, a carboxyl group, an alkoxy group, an aryloxy group, a silyloxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group or a silyl group and the like. Further, if the aryl group has a substituent group, they may form a ring like a carbazole. $R_1$ and $R_2$ may also have a substituent group, and examples of the further substituent group include the substituent groups described above.

Wherein, if the number of carbon atoms of the groups $R_1$ and $R_2$ represent is too small, the solubility of the compound of Formula (I) in a solvent (a solvent used in the coating liquid when preparing an organic nonlinear optical material a wet coating) is lowered and may not be applied homogeneously, on the other hand, if the number is too large, the nonlinear optical active ingredient per unit weight is lowered. Therefore, the substituted or unsubstituted alkyl group $R_1$ and $R_{11}$ represent preferably has 4 to 20 carbon atoms, and the substituted or unsubstituted aryl group preferably has 6 to 30 carbon atoms.

$R_1$ and $R_2$, each independently, represent preferably a substituted ethyl group, a substituted butyl group, a substituted hexyl group, a substituted 2-ethylhexyl group, more preferably a substituted ethyl group, a substituted butyl group, and a substituted hexyl group, and still more preferably, an acyloxy group substituted ethyl group, an acyloxy group substituted butyl group, an acyloxy group substituted hexyl group, an alkoxy group substituted ethyl group, an alkoxy group substituted butyl group, an alkoxy group substituted hexyl group.

In Formula (I), $R_3$ represents a hydrogen atom, a substituted or unsubstituted alkyl group, or a substituted or unsubstituted aryl group.

The alkyl group may include alkyl groups that the above mentioned $R_1$ and $R_2$ may take, preferably a methyl group, an ethyl group, an n-propyl group, an i-propyl group, an n-butyl group, a t-butyl group, an n-hexyl group, and 2-ethylhexyl group, and more preferably an ethyl group, an n-butyl group, and an n-hexyl group.

The aryl group may include aryl groups that the above mentioned $R_1$ and $R_2$ may take, and preferably a phenyl group.

The alkyl group and the aryl group may have a substituent group, and the substituent group may include substituent groups that the above mentioned $R_1$ and $R_2$ may have, and preferably a halogen atom, an alkoxy group, an aryl group and an alkoxycarbonyl group.

$R_3$ is preferably a hydrogen atom or a substituted or unsubstituted alkyl group having 30 carbon atoms or less and more preferably a substituted or unsubstituted alkyl group having 20 carbon atoms or less from the viewpoint of improving solubility of the compound and suppressing aggregation between molecules, and the substituent group of the substituted alkyl group is preferably an acyloxy group or an alkoxy group.

In Formula (I), L connects a nitrogen atom and an oxopyrroline ring having a dicyanomethylidene group in π-conjugated system, and L represents a divalent linking group containing an azo group (—N=N—) in the α-conjugated system. Since L contains an azo group, it may reduce the number of sites (=CH—) containing high reactive methine hydrogen from the π-conjugated system, which leads to improving the stability to light and heat, for example, as compared with cyanine backbone. The number of azo groups in L is preferably from 1 to 4, and more preferably 1, or 2 or less from the viewpoint of ensuring the cohesion resistance properties and solubility in a solvent (a solvent used for the coating liquid when producing an organic nonlinear optical material by a wet coating).

The compound of Formula (I) may be preferably a compound represented by the following Formula (II).

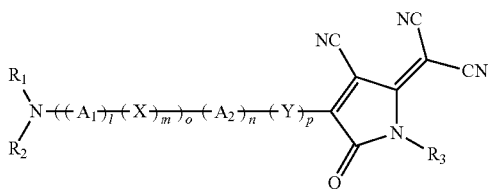

Formula (II)

(In Formula (II), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$A_1$ and $A_2$ each independently represent a substituted or unsubstituted aromatic group.

X represents —$CR_4$=$CR_5$—, —C≡C—, —$CR_6$=N—, —N=$CR_7$—, or —N=N—.

Y represents —$CR_8$=$CR_9$—, or a substituted or unsubstituted aromatic group.

$R_4$, $R_5$, $R_6$, $R_7$, $R_8$ and $R_9$ each independently represent a hydrogen atom, a substituted or unsubstituted alkyl group, or a substituted or unsubstituted aryl group.

l and n each independently represent an integer of 0 to 3.

m, o, and p each independently represent an integer of 1 to 3.

Each $R_4$, $R_5$, $R_6$, $R_7$, $R_8$, $R_9$, $A_1$, $A_2$, X, Y, l and m may be the same or different, and at least one of X contains —N=N—.)

In Formula (II), $R_1$, $R_2$ and $R_3$ have the same meaning as $R_1$, $R_2$ and $R_3$ in Formula (I), and preferred examples of each are the same.

In Formula (II), $A_1$ and $A_2$ each independently represent a substituted or unsubstituted aromatic group.

Examples of the aromatic group include a phenylene group, naphthylene group and the like. Further, the aromatic group may be a heteroaromatic group.

Specific examples of the heterocyclic aromatic group include a divalent pyridine ring, a pyrazine ring, pyridazine ring, a pyrimidine ring, a triazine ring, a quinoline ring, an isoquinoline ring, a quinazoline ring, a cinnoline ring, a phthalazine ring, a quinoxaline ring, a pyrrole ring, an indole ring, a furan ring, a benzofuran ring, a thiophene ring, a benzothiophene ring, a pyrazole ring, an imidazole ring, a benzimidazole ring, a triazole ring, an oxazole ring, a benzoxazole ring, a thiazole ring, a benzothiazole ring, an isothiazole ring, a benzisothiazole ring, a thiadiazole ring, an isoxazole ring, and the benzisoxazole ring.

The heterocyclic aromatic group is preferably 5- or 6-membered heterocyclic aromatic group and the hetero atom for the ring configuration is preferably an oxygen atom, a sulfur atom, or a nitrogen atom. The heterocyclic aromatic group is more preferably 5- or 6-membered heterocyclic aromatic group having 3 to 30 carbon atoms and the hetero atom for the ring configuration is more preferably a sulfur atom, or a nitrogen atom.

The above mentioned aromatic group may have a substituent group, and examples of the substituent group may include an additional substituent in case the above described $R_1$ and $R_2$ have a substituent group.

$A_1$ is preferably a substituted aryl group or a 5- or 6-membered heterocyclic aromatic group containing any one of an oxygen atom, a sulfur atom, and a nitrogen atom as a hetero atom, more preferably a phenylene group, a naphthylene group, a divalent thiophene ring (a thienylene group), a divalent pyrrole ring, a divalent furan ring, still more preferably a phenylene group, a thienylene group, or a divalent pyrrole ring, and particularly far more preferably a phenylene group.

Since in the compound whose $A_1$ is unsubstituted, its raw material cost is cheaper and the number of steps of the synthesis is small until the end of the process, the manufacturing cost of the compound may be suppressed. On the other hand, since in the compound having a substituent group in $A_1$, the bleed-out during the formation of the thin film of the organic nonlinear optical material may be suppressed, the yield of manufacturing the device production is improved.

The substituent group in the case that $A_1$ has a substituent group may be singular or plural, preferably a substituted or unsubstituted alkyl group having 1 to 30 carbon atoms, a substituted or unsubstituted aryl having 6 to 30 carbon atoms, a substituted or unsubstituted heteroaryl group having 5 to 30 carbon atoms, a substituted or unsubstituted alkoxy group having 1 to 30 carbon atoms, a substituted or unsubstituted alkylthio group having 1 to 30 carbon atoms, a substituted or unsubstituted carbamoyl group having 2 to 30 carbon atoms or a substituted or unsubstituted acylamino group having 2 to 30 carbon atoms, and more preferably a substituted or unsubstituted alkyl group having 1 to 20 carbon atoms, a substituted or unsubstituted alkoxy group having 1 to 20 carbon atoms, a substituted or unsubstituted alkylthio group having 1 to 20 carbon atoms, or a substituted or unsubstituted acylamino group having 3 to 30 carbon atoms.

$A_2$ is preferably a 5- or 6-membered heterocyclic aromatic group containing any one of an oxygen atom, a sulfur atom, and a nitrogen atom as a hetero atom, more preferably a phenylene group, a naphthylene group, a divalent thiophene ring (a thienylene group), a divalent pyrrole ring, or a divalent thiazole ring, and far more preferably a thienylene group, a divalent thiazole ring or a phenylene group.

Also, $A_2$ may have a substituent group, and the substituent group is preferably a halogen atom, a cyano group, a substituted or unsubstituted alkyl group, a substituted or unsubstituted aryl group, a substituted or unsubstituted alkyl group, a substituted or unsubstituted heteroaryl group, a substituted or unsubstituted alkoxy group, a substituted oxycarbonyl group, a substituted acyl group, or a substituted or unsubstituted carbamoyl group, and more preferably a cyano group, a substituted or unsubstituted alkyl group, a substituted or unsubstituted aryl group, a substituted or unsubstituted alkoxy group, a substituted oxycarbonyl group, or a substituted acyl group.

In Formula (II), l represents an integer of 0 to 3. l is preferably 1 or 2.

In Formula (II), n represents an integer of 0 to 3. n preferably represents an integer of 1 to 3 in order to increase the nonlinear optical performance of the compound. Further, it is more preferably an integer of 1 or 2 in consideration of the balance with the cohesion resistance of the compound.

In Formula (II), X represents —$CR_4$=$CR_5$—, —C≡C—, —$CR_6$=N—, —N=$CR_7$—, or —N=N—. At least one of X contains —N=N—.

$R_4$, $R_5$, $R_6$ and $R_7$ each independently represent a hydrogen atom, a substituted or unsubstituted alkyl group, or a substituted or unsubstituted aryl group.

Examples of the alkyl group and the aryl group as $R_4$, $R_5$, $R_6$ and $R_7$, and the substituent group that these groups may have the same meaning as the alkyl group and the aryl group as $R_1$ and $R_2$, and the substituent group that these groups may have.

$R_4$, $R_5$, $R_6$ and $R_7$ are preferably a hydrogen atom, a substituted or unsubstituted alkyl group having 20 or less carbon atoms, or a substituted or unsubstituted alkyl group having 6 to 30 carbon atoms, and more preferably a hydrogen atom.

X is preferably —$CR_4$=$CR_5$— or —N=N—, if there are a plurality of X, all Xs are particularly preferably —N=N— from the viewpoint of improving stability.

In Formula (II), m represents an integer of 1 to 3, and is preferably 1.

In Formula (II), o represents an integer of 1 to 3, and is preferably 1 or 2. The larger o raises more potential of the nonlinear optical activity of the compound, but if it is too large, since it promotes aggregation between molecules and the potential cannot be exerted, it is not desirable.

In Formula (II), Y represents —$CR_8$=$CR_9$—, or a substituted or unsubstituted aromatic group. $R_8$ and $R_9$ each independently represent a hydrogen atom, a substituted or unsubstituted alkyl group, or a substituted or unsubstituted aryl group.

The aromatic group may be a heterocyclic aromatic group, and examples of an aromatic group and the substituent group the aromatic group may have are the same as an aromatic group as $A_1$ and $A_2$, and the substituent group the aromatic group may have.

Examples of the alkyl group and the aryl group as $R_8$ and $R_9$ and the substituent group that these groups may have the same meaning as the alkyl group and the aryl group as $R_4$, $R_5$, $R_6$ and $R_7$ and the substituent group that these groups may have. If there are a plurality of $R_8$ and $R_9$, these groups may be linked to each other to form a ring. The preferred groups as $R_8$ and $R_9$ are the same as the preferred groups as $R_4$, $R_5$, $R_6$ and $R_7$.

Y is preferably —$CR_8$=$CR_9$— or a heterocyclic aromatic group from the viewpoint of both stability and nonlinear optical activity, and particularly preferably —$CR_8$=$CR_9$— or a substituted or unsubstituted thienylene group.

In Formula (II), p represents an integer of 1 to 3, and is preferably 1 or 2.

In Formula (II), $A_1$ represents a substituted or unsubstituted phenylene group, X represents —N=N—, l and m represent 1, n and p represent an integer satisfying the formula, 2≤n+p≤3, and more preferably, $A_2$ represents any one of the shown below.

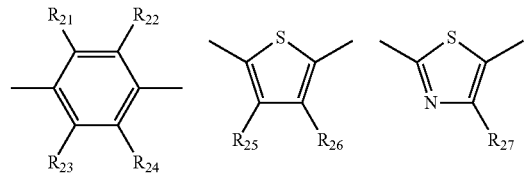

($R_{21}$, $R_{22}$, $R_{23}$ and $R_{24}$ each independently represent a hydrogen atom, a halogen atom, a cyano group, a substituted or unsubstituted alkyl group, a substituted or unsubstituted aryl group, a substituted or unsubstituted heteroaryl group, a substituted or unsubstituted alkoxy group, a substituted acyl group or a substituted or unsubstituted carbamoyl group, $R_{25}$ and $R^{26}$ each independently represent a hydrogen atom, a halogen atom, a cyano group, a substituted or unsubstituted alkyl group, a substituted or unsubstituted aryl group, a substituted or unsubstituted heteroaryl group, a substituted or unsubstituted alkoxy group or a substituted acyl group, $R_{27}$ represents a hydrogen atom, a halogen atom, a cyano group, a substituted or unsubstituted alkoxy group, a substituted or unsubstituted alkyl group, a substituted or unsubstituted aryl group, a substituted or unsubstituted heteroaryl group, or a substituted oxycarbonyl group. Each $R_{21}$, $R_{22}$, $R_{23}$, $R_{24}$, $R_{25}$, $R_{26}$ and $R_{27}$ may be the same or different, and $R_{21}$ and $R_{22}$, $R_{23}$ and $R_{24}$, or $R_{25}$ and $R_{26}$ may be linked to each other to form a ring.)

$R_{21}$, $R_{22}$, $R_{23}$ and $R_{24}$ are each independently preferably a hydrogen atom, a cyano group, a substituted or unsubstituted alkyl group having 1 to 30 carbon atoms, a substituted or unsubstituted aryl group having 6 to 30 carbon atoms, a substituted or unsubstituted alkoxy group having 1 to 30 carbon atoms or a substituted acyl group having 2 to 30 carbon atoms, and more preferably a hydrogen atom, a substituted or unsubstituted alkyl group having 1 to 15 carbon atoms or a substituted acyl group having 2 to 20 carbon atoms.

$R_{25}$ and $R_{26}$ are preferably a hydrogen atom, a cyano group, a substituted or unsubstituted alkyl group having 1 to 30 carbon atoms, a substituted or unsubstituted aryl group having 6 to 30 carbon atoms, a substituted or unsubstituted alkoxy group having 1 to 30 carbon atoms or a substituted acyl group having 2 to 30 carbon atoms, and more preferably a hydrogen atom, a cyano group, a substituted or unsubstituted alkyl group having 1 to 15 carbon atoms, a substituted or unsubstituted aryl group having 6 to 20 carbon atoms, an unsubstituted alkoxy group having 4 to 15 carbon atoms or the group to form a ring or to from a 6- to 12-membered ring containing an oxygen atom.

$R_{27}$ is preferably a hydrogen atom, a cyano group, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms or a substituted oxycarbonyl group having 2 to 30 carbon atoms, and more preferably a hydrogen atom, a substituted or unsubstituted alkyl group having 1 to 15 carbon atoms or a substituted or unsubstituted aryl group having 6 to 20 carbon atoms.

The present invention also relates to a compound represented by Formula (II).

Since the compound represented by Formula (II) has a nonlinear optical activity, it is useful as a nonlinear optical material.

The compound represented by the above mentioned Formula (II) is more preferably the compound represented by Formula (III).

In Formula (III), $R_{11}$ and $R^{12}$ each independently represent a hydrogen atom, a substituted or unsubstituted alkyl group, or a substituted or unsubstituted alkoxy group. $R_{11}$ and $R_{12}$ may be linked to each other to form a ring.

The alkyl group may include an n-butyl group, an n-hexyl group, an n-octyl group and the like, preferably an alkyl group having 1 to 20 carbon atoms, and more preferably an alkyl group having 4 to 15 carbon atoms.

The alkoxy group may include a methoxy group, an ethoxy group, an n-butyloxy group, an n-hexyloxy group and the like, preferably an alkoxy group having 1 to 20 carbon atoms, and more preferably an unsubstituted alkoxy group having 4 to 15 carbon atoms or the group to form a ring or to from a 6- to 12-membered ring containing an oxygen atom.

Examples of the substituent group that the alkyl group and the alkoxy group may have include an acyloxy group, an oxycarbonyl group, an aryl group and the like.

$R_{11}$ and $R_{12}$ are preferably a hydrogen atom, a substituted or unsubstituted alkyl group having 1 to 20 carbon atoms, or a substituted or unsubstituted alkoxy group having 1 to 20 carbon atoms, and more preferably a hydrogen atom, an unsubstituted alkyl group having 4 to 15 carbon atoms, an

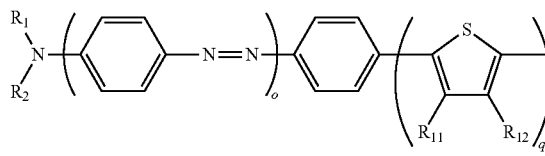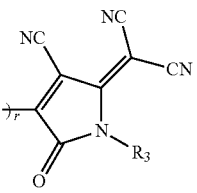

Formula (III)

(In Formula (III), $R_1$ and $R_2$ each independently represent a substituted or unsubstituted alkyl group or a substituted or unsubstituted aryl group.

$R_3$ represents a hydrogen atom, a substituted or unsubstituted alkyl group or a substituted or unsubstituted aryl group.

o represents an integer of 1 to 3.

$R_{11}$ and $R_{12}$ each independently represent a hydrogen atom, a substituted or unsubstituted alkyl group or a substituted or unsubstituted alkoxy group. They may be linked to each other to form a ring.

q and r each independently represent 0 or 1. However, q and r will not be 0 at the same time.)

$R_1$, $R_2$, $R_3$ and o in Formula (III) are the same as $R_1$, $R_2$, $R_3$ and o in Formula (II), and the preferred examples of each are the same.

unsubstituted alkoxy group having 4 to 15 carbon atoms. $R_{11}$ and $R_{12}$ may be liked to each other to form a ring, and when they form a ring, they may preferably form a 6- to 12-membered ring containing an oxygen atom.

Moreover, the compound represented by the above mentioned Formula (II) is more preferably the compound represented by Formula (IV).

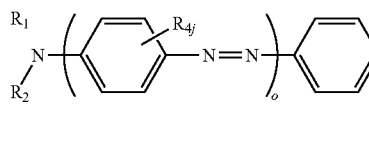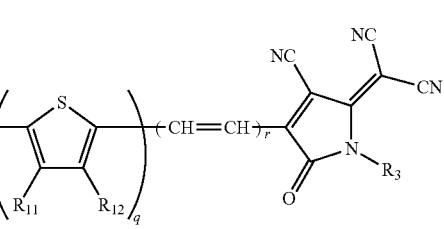

Formula (IV)

(In Formula (IV), $R_1$ and $R_2$ each independently represent a substituted or unsubstituted alkyl group or a substituted or unsubstituted aryl group.

$R_3$ represents a hydrogen atom, a substituted or unsubstituted alkyl group, or a substituted or unsubstituted aryl group.

$R_{4j}$ represents a substituted or unsubstituted alkyl group, a substituted or unsubstituted aryl group, a substituted or unsubstituted heteroaryl group, a substituted or unsubstituted alkoxy group, a substituted or unsubstituted alkylthio group, a substituted or unsubstituted carbamoyl group, or a substituted or unsubstituted acylamino group, $R_{4j}$ may be singular or plural, and each $R_{4j}$ may be the same or different.

o represents an integer of 1 to 3.

$R_{11}$ and $R_{12}$ each independently represent a hydrogen atom, a substituted or unsubstituted alkyl group or a substituted or unsubstituted alkoxy group. They may be linked to each other to form a ring.

q and r each independently represent 0 or 1. However, q and r will not be 0 at the same time.)

$R_1$, $R_2$, $R_3$ and o in Formula (IV) are the same as $R_1$, $R_2$, $R_3$ and o in Formula (II), and the preferred examples thereof are also the same.

In Formula (IV), $R_{11}$ and $R_{12}$ each independently represent a hydrogen atom, a substituted or unsubstituted alkyl group, or a substituted or unsubstituted alkoxy group. $R_{11}$ and $R_{12}$ may be linked to each other to form a ring.

The alkyl group may include an n-butyl group, an n-hexyl group, an n-octyl group and the like, preferably an alkyl group having 1 to 20 carbon atoms, and more preferably an alkyl group having 4 to 15 carbon atoms.

The alkoxy group may include a methoxy group, an ethoxy group, an n-butyloxy group, an n-hexyloxy group and the like, preferably an alkoxy group having 1 to 20 carbon atoms, and more preferably an unsubstituted alkoxy group having 4 to 15 carbon atoms or the group to form a ring or to from a 6- to 12-membered ring containing an oxygen atom.

Examples of the substituent group that the alkyl group and the alkoxy group may have include an acyloxy group, an oxycarbonyl group, an aryl group and the like.

$R_{11}$ and $R_{12}$ are preferably a hydrogen atom, a substituted or unsubstituted alkyl group having 1 to 20 carbon atoms, or a substituted or unsubstituted alkoxy group having 1 to 20 carbon atoms, and more preferably a hydrogen atom, an unsubstituted alkyl group having 4 to 15 carbon atoms, an unsubstituted alkoxy group having 4 to 15 carbon atoms or the group to form a ring or to from a 6- to 12-membered ring containing an oxygen atom.

$R_{4j}$ may be singular or plural, and may be preferably a substituted or unsubstituted alkyl group having 1 to 30 carbon atoms, a substituted or unsubstituted aryl group having 6 to 30 carbon atoms, a substituted or unsubstituted heteroaryl group having 5 to 30 carbon atoms, a substituted or unsubstituted alkoxy group having 1 to 30 carbon atoms, a substituted or unsubstituted alkylthio group having 1 to 30 carbon atoms, a substituted or unsubstituted carbamoyl group having 2 to 30 carbon atoms, or a substituted or unsubstituted acylamino group having 2 to 30 carbon atoms, and more preferably a substituted or unsubstituted alkyl group having 1 to 20 carbon atoms, a substituted or unsubstituted alkoxy group having 1 to 20 carbon atoms, a substituted or unsubstituted alkylthio group having 1 to 20 carbon atoms, or a substituted or unsubstituted acylamino group having 3 to 30 carbon atoms, and still more preferably a substituted or unsubstituted alkyl group having 1 to 20 carbon atoms or a substituted, or unsubstituted alkoxy group having 1 to 20 carbon atoms. Further, $R_{4j}$ is more preferably singular than plural.

The substituent group $R_{4j}$ may also have is preferably an acyloxy group, an oxycarbonyl group, an aryl group, a heteroaryl group or a silyloxyl group.

Further, the compound represented by the above mentioned Formula (II) is more preferably the compound represented by Formula (V).

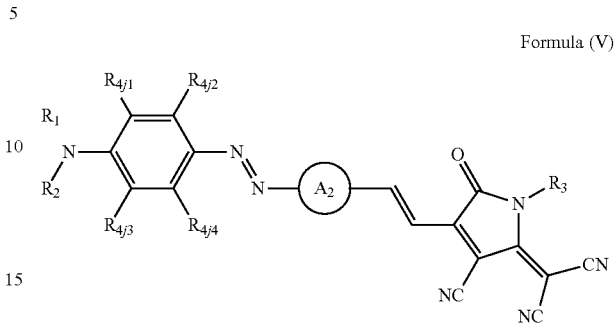

Formula (V)

(In Formula (V), $R_1$ and $R_2$ each independently represent a substituted or unsubstituted alkyl group or a substituted or unsubstituted aryl group.

$R_3$ represents a hydrogen atom, a substituted or unsubstituted alkyl group or a substituted or unsubstituted aryl group.

$R_{4j1}$ to $R_{4j4}$ each independently represent a hydrogen atom, a substituted or unsubstituted alkyl group, a substituted or unsubstituted aryl group, a substituted or unsubstituted heteroaryl group, a substituted or unsubstituted alkoxy group, a substituted or unsubstituted alkylthio group, a substituted or unsubstituted carbamoyl group, or a substituted or unsubstituted acylamino group.

$A_2$ represents a substituted or unsubstituted an aromatic group.)

$A_2$, $R_1$, $R_2$ and $R_3$ in Formula (V) are the same as $A_2$, $R_1$, $R_2$ and $R_3$ in Formula (II), and the preferred examples of each are the same.

$R_{4j1}$ to $R_{4j4}$ in Formula (V) each independently represent a hydrogen atom or the same substituent group as $R_{4j}$ in Formula (IV), and are preferably a hydrogen atom, a substituted or unsubstituted alkyl group having 1 to 30 carbon atoms, a substituted or unsubstituted aryl group having 6 to 30 carbon atoms, a substituted or unsubstituted heteroaryl group having 5 to 30 carbon atoms, a substituted or unsubstituted alkoxy group having 1 to 30 carbon atoms, a substituted or unsubstituted alkylthio group having 1 to 30 carbon atoms, a substituted or unsubstituted carbamoyl group having 2 to 30 carbon atoms, or a substituted or unsubstituted acylamino group having 2 to 30 carbon atoms, and more preferably, a hydrogen atom, a substituted or unsubstituted alkyl group having 1 to 20 carbon atoms, a substituted or unsubstituted alkoxy group having 1 to 20 carbon atoms, a substituted or unsubstituted alkylthio group having 1 to 20 carbon atoms, or a substituted or unsubstituted acylamino group having 3 to 30 carbon atoms, and far more preferably a hydrogen atom, a substituted or unsubstituted alkyl group having 1 to 20 carbon atoms, or a substituted or unsubstituted alkoxy group having 1 to 20 carbon atoms.

Hereinafter, specific examples of the organic compound having a nonlinear optical activity represented by Formula (I) to (V) used in the present invention will be described. However, the scope of the present invention is not limited only thereto.

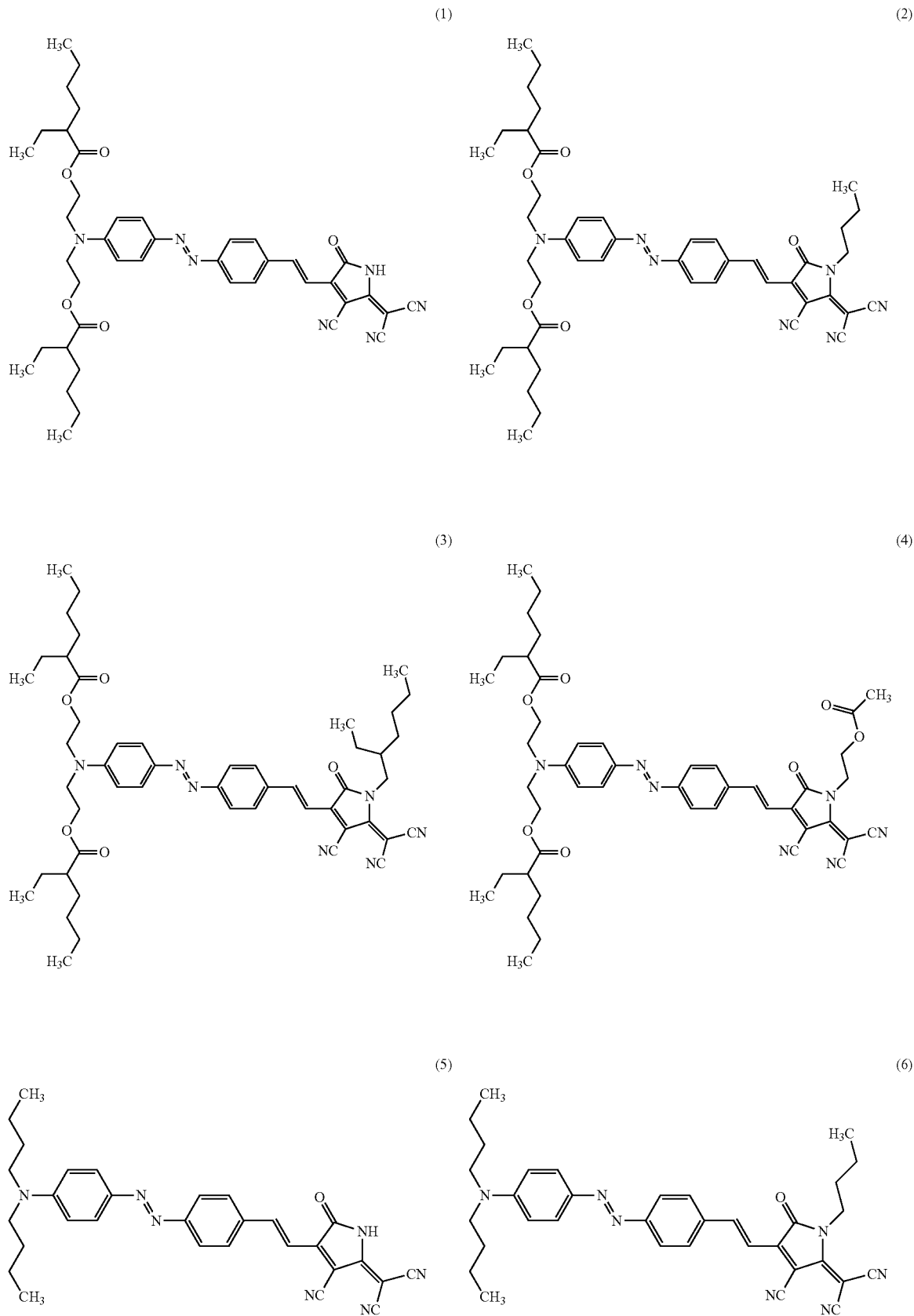

-continued
(7)
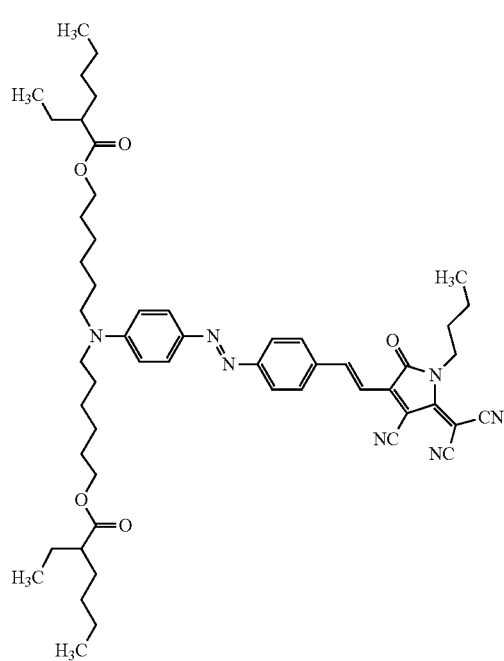
(8)
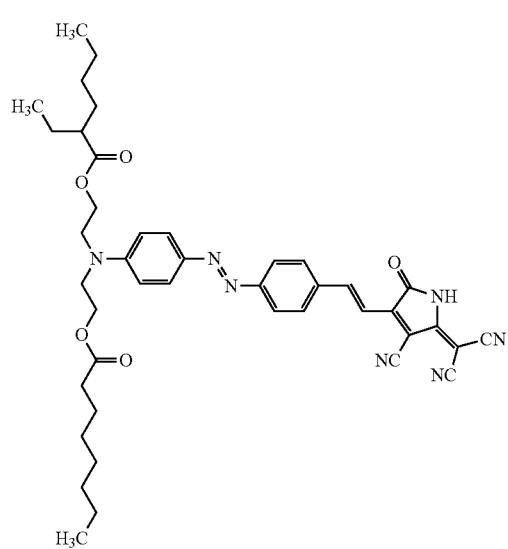
(9)
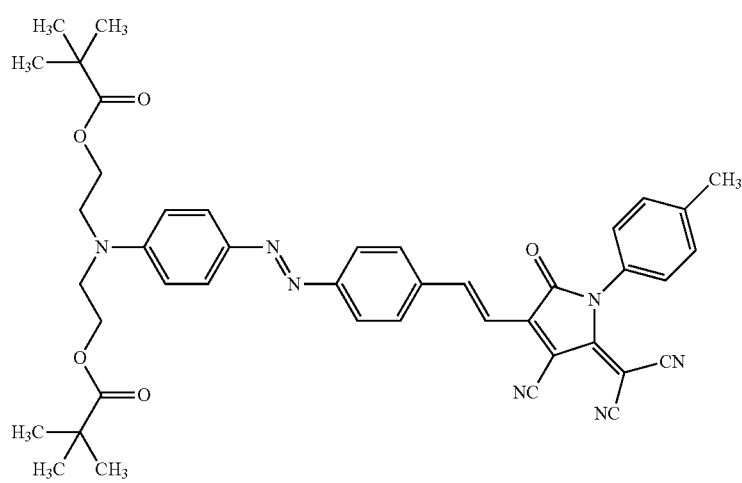
(10)
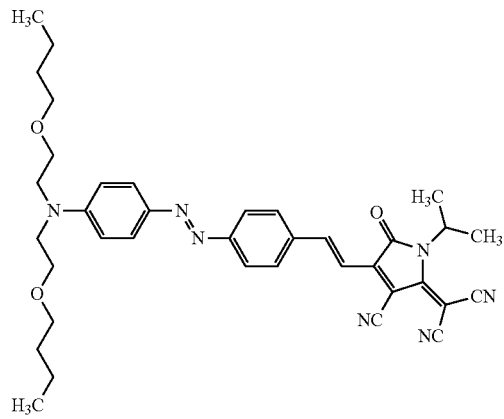
(11)
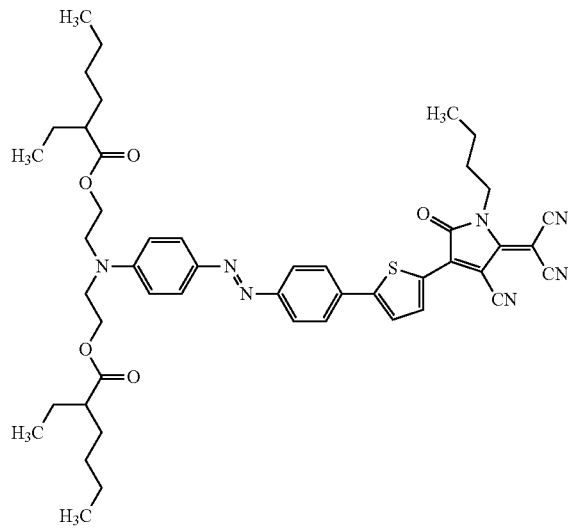

-continued
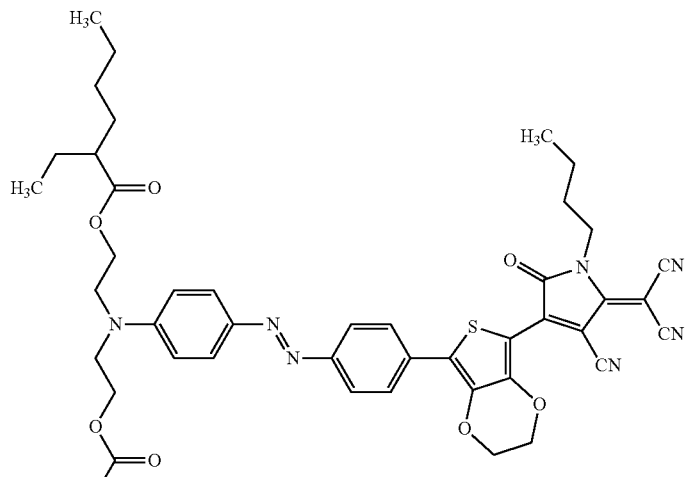
(12)
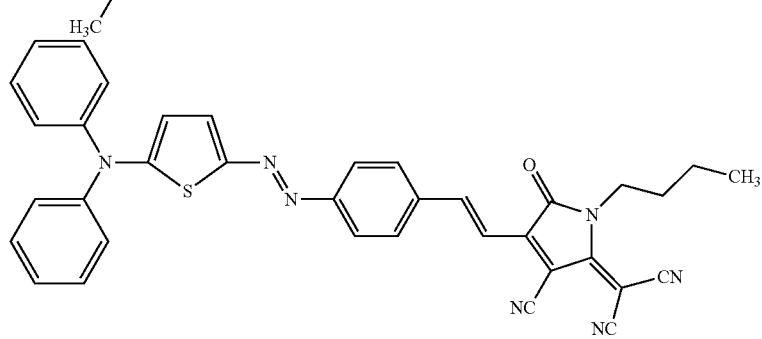
(13)
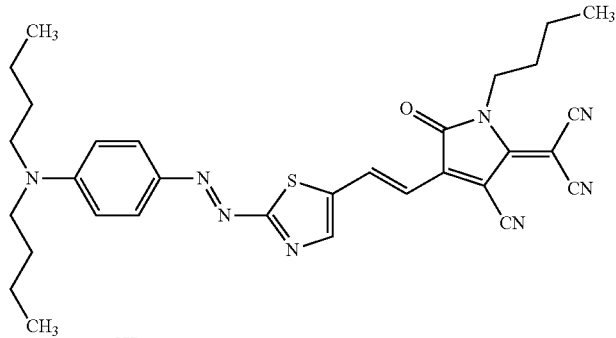
(14)
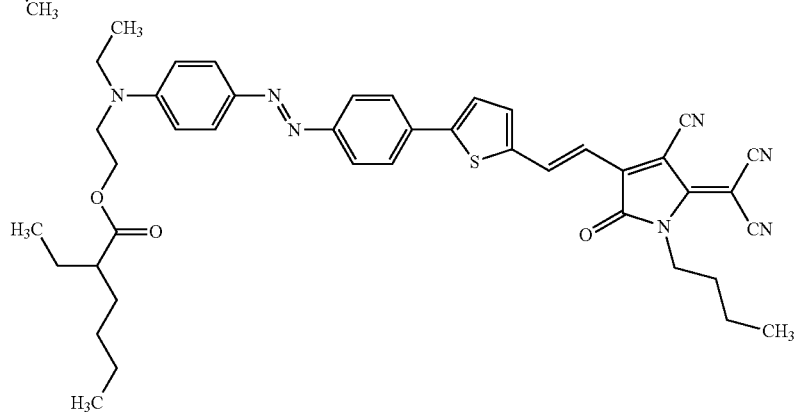
(15)

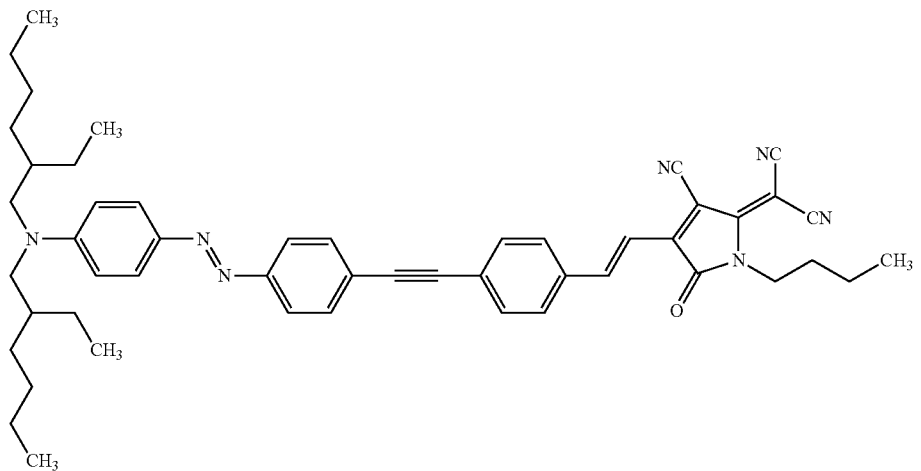
(16)
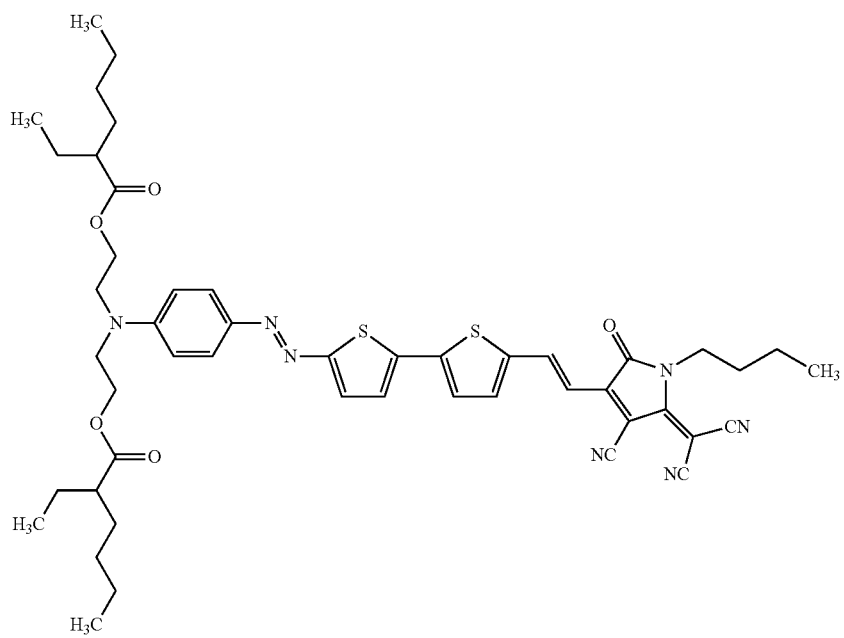
(17)
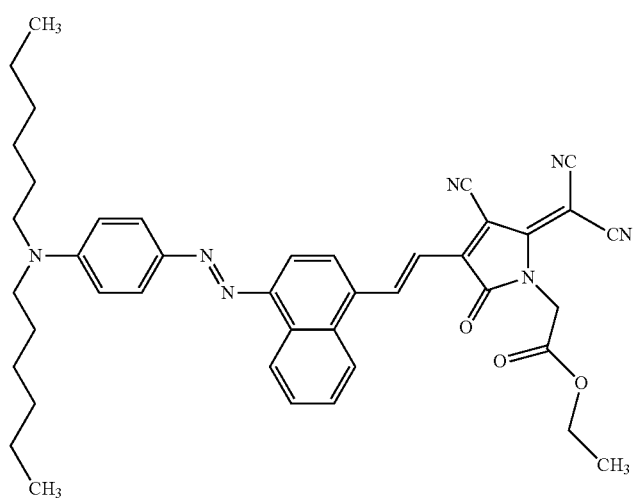
(18)

-continued
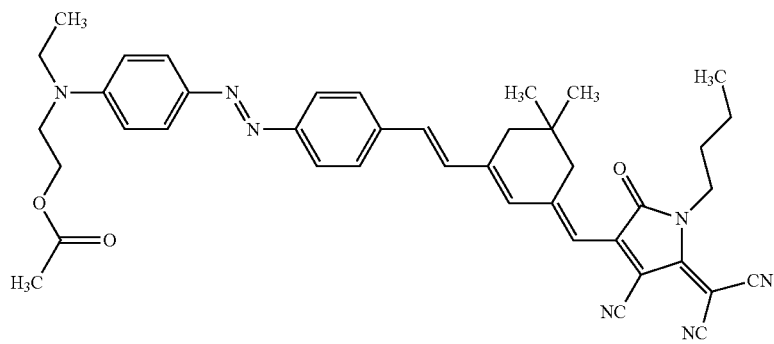
(19)
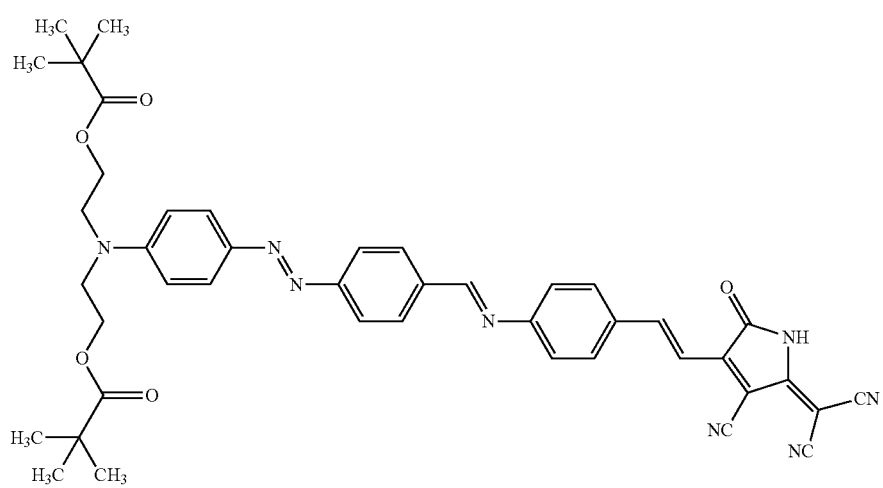
(20)
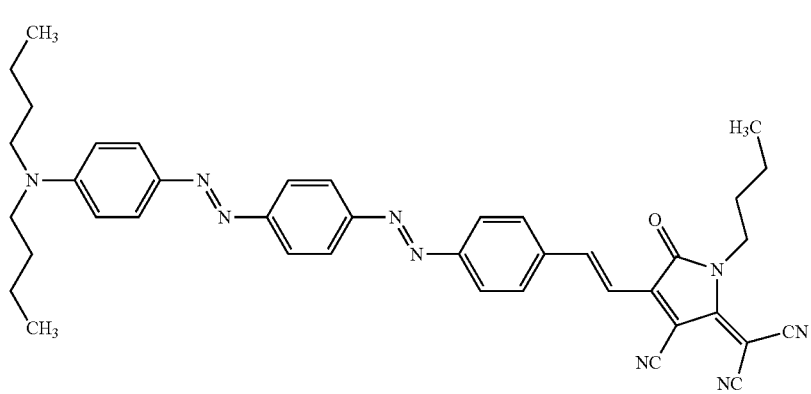
(21)
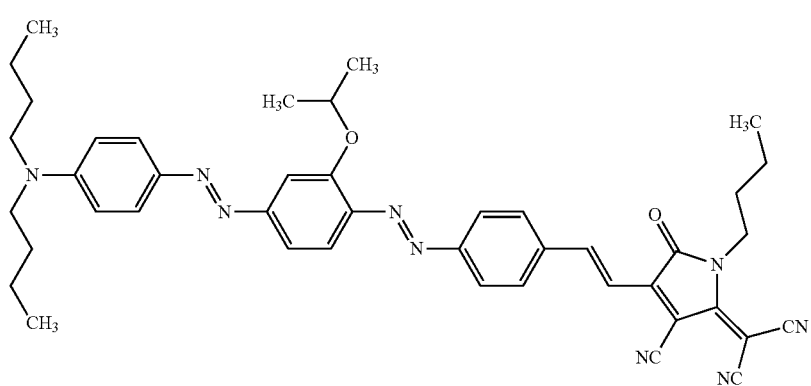
(22)

(23)
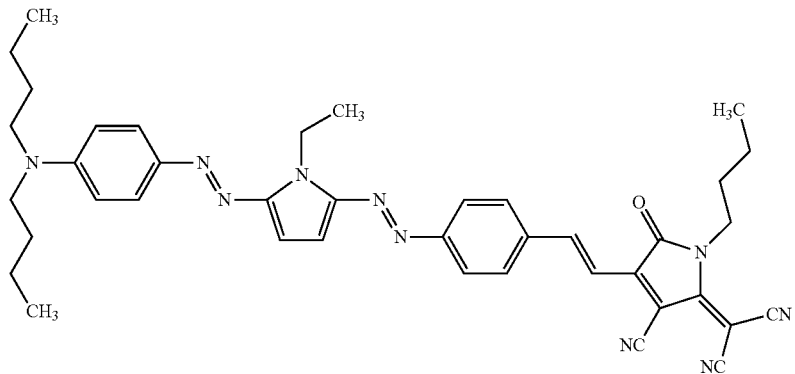
(24)
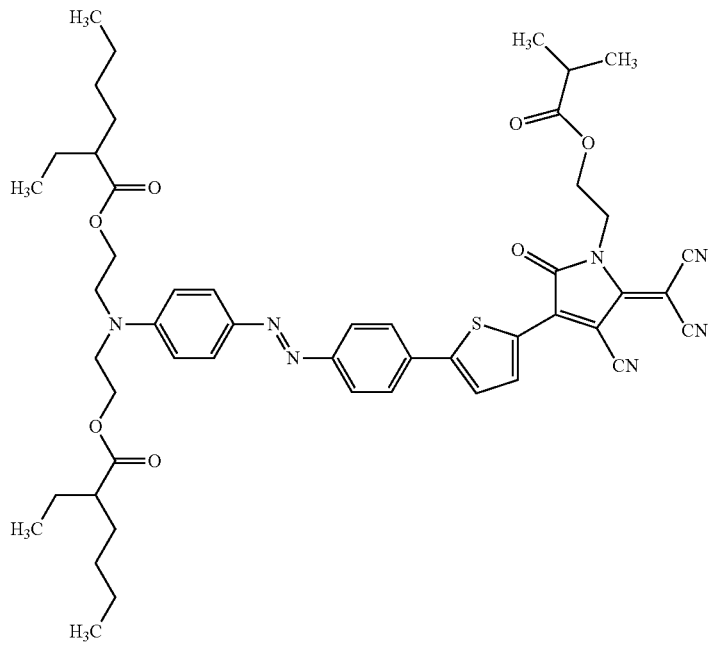
(25)
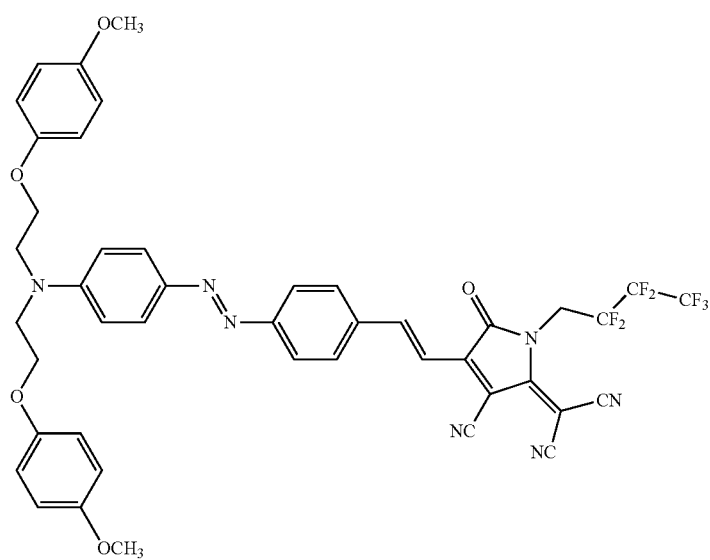

-continued
(26)
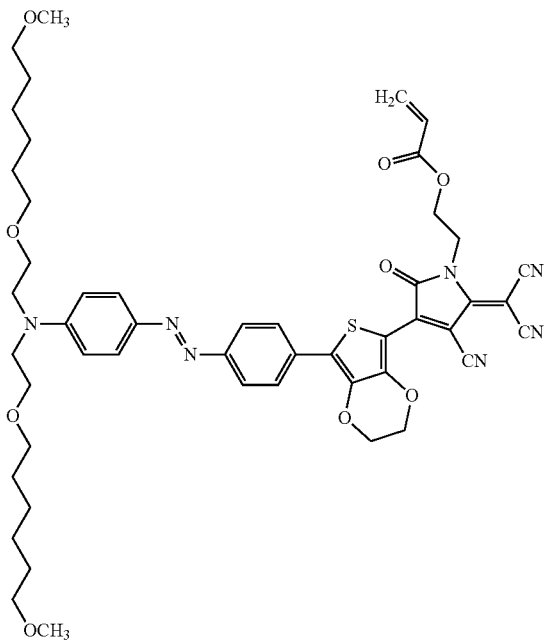
(27)
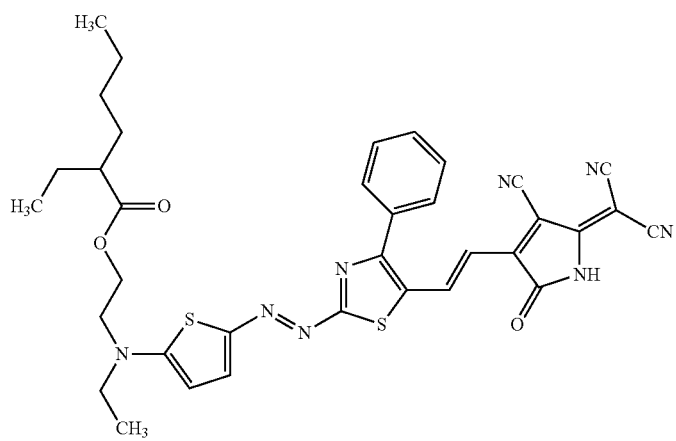
(28)
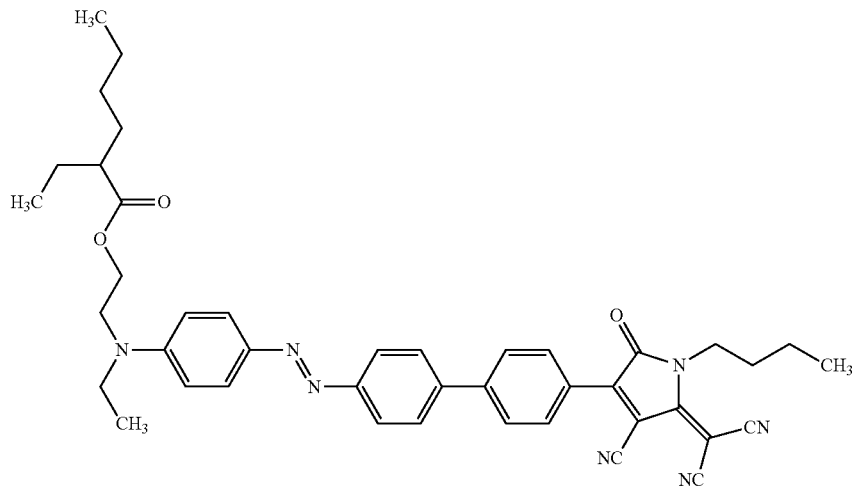

| No. | R1 | R2 | R4j1 | R4j2 | R4j3 | R4j4 | A2 | R3 |
|---|---|---|---|---|---|---|---|---|
| 29 | n-Bu | n-Bu | H | H | H | H |  | n-Bu |
| 30 | n-Bu | n-Bu | H | H | H | H |  |  |
| 31 |  |  | H | H | H | H |  | H |
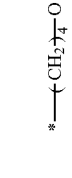

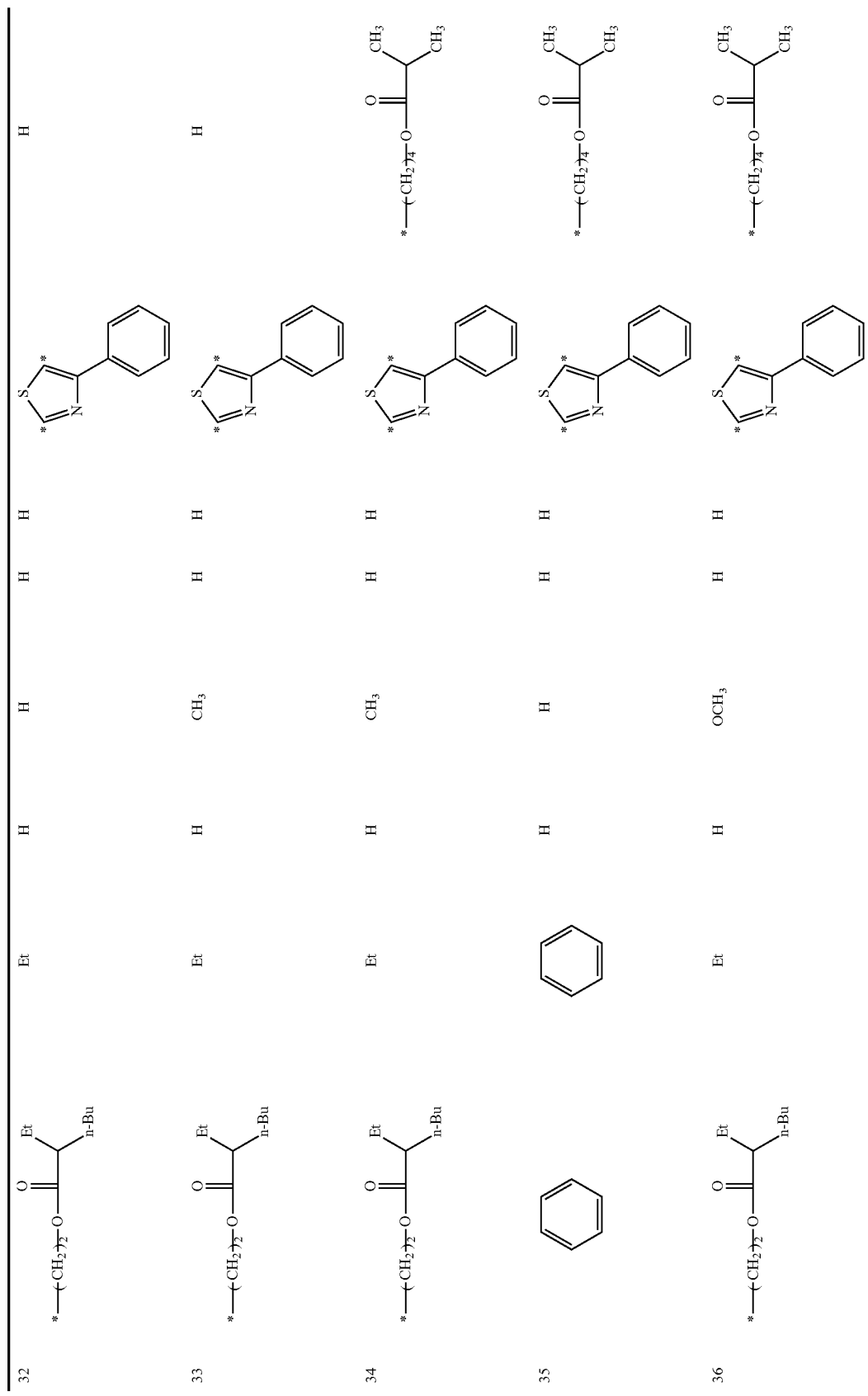

| | | | | | |
|---|---|---|---|---|---|
| 37 | *-(CH$_2$)$_2$-O-C(O)-CH(Et)(n-Bu) | Et | H | SCH$_3$ | H | *-thiazole-Ph (4-phenylthiazol-2-yl) | n-Hex |
| 38 | *-(CH$_2$)$_2$-O-C(O)-CH(Et)(n-Bu) | Et | H | *-NH-C(O)-CH(Et)(n-Bu) | H | *-thiazole-Ph | *-(CH$_2$)$_4$-O-C(O)-CH(CH$_3$)$_2$ |
| 39 | n-Hex | n-Hex | H | *-C(O)-NH-Et | H | *-thiazole-Ph | *-(CH$_2$)$_4$-O-C(O)-CH(Et)(n-Bu) |
| 40 | *-(CH$_2$)$_2$-O-C(O)-CH(Et)(n-Bu) | Et | H | *-O-CH$_2$-CH(Et)(n-Bu) | H | *-thiazole-Ph | *-(CH$_2$)$_4$-O-C(O)-CH(CH$_3$)$_2$ |
| 41 | *-(CH$_2$)$_2$-O-C(O)-CH(Et)(n-Bu) | Et | H | H | H | *-thiazole-C(O)-O-Et | *-(CH$_2$)$_4$-O-C(O)-CH(CH$_3$)$_2$ |

| | | | | | | |
|---|---|---|---|---|---|---|
| 42 | *−(CH₂)₂−O−C(=O)−CH(Et)(n-Bu) | Et | H | H | H | thiazole-CH₃ | *−(CH₂)₄−O−C(=O)−CH(CH₃)₂ |
| 43 | *−(CH₂)₂−O−C(=O)−CH(Et)(n-Bu) | Et | H | *−O−CH₂−CH(Et)(n-Bu) | H | thiazole-CH₃ | *−(CH₂)₄−O−C(=O)−CH(CH₃)₂ |
| 44 | *−(CH₂)₂−O−C(=O)−CH(Et)(n-Bu) | Et | H | H | H | thiazole | *−(CH₂)₄−O−C(=O)−CH(CH₃)₂ |
| 45 | *−(CH₂)₂−O−C(=O)−CH(Et)(n-Bu) | Et | H | *−O−CH₂−CH(Et)(n-Bu) | H | thiazole | *−(CH₂)₄−O−C(=O)−CH(CH₃)₂ |
| 46 | *−(CH₂)₂−O−C(=O)−CH(Et)(n-Bu) | *−(CH₂)₂−O−C(=O)−CH(Et)(n-Bu) | H | H | H | phenyl | *−(CH₂)₄−O−C(=O)−CH(CH₃)₂ |
| 47 | *−(CH₂)₂−O−C(=O)−CH(Et)(n-Bu) | Et | H | CH₃ | H | phenyl | *−(CH₂)₄−O−C(=O)−CH(CH₃)₂ |
| 48 | *−(CH₂)₂−O−C(=O)−CH(Et)(n-Bu) | Et | H | CH₃ | CH₃ | phenyl | *−(CH₂)₄−O−C(=O)−CH(CH₃)₂ |
| 49 | *−(CH₂)₂−O−CH₂−(CH₂)₃−OCH₃ | Et | H | H | H | phenyl | *−(CH₂)₄−O−C(=O)−CH(Et)(n-Bu) |

-continued

| | | | | | | |
|---|---|---|---|---|---|---|
| 50 | *-(CH₂)₂-O-C(=O)-CH(Et)(n-Bu) | Et | *-NH-C(=O)-CH(Et)(n-Bu) | H | phenyl (* at one position) | H | n-Bu |
| 51 | *-(CH₂)₂-O-C(=O)-CH(Et)(n-Bu) | *-(CH₂)₂-O-C(=O)-CH(Et)(n-Bu) | OCH₃ | H | phenyl (* at one position) | H | H |
| 52 | *-(CH₂)₂-O-C(=O)-CH(Et)(n-Bu) | Et | H | H | o-methylphenyl | H | n-Bu |
| 53 | *-(CH₂)₂-O-C(=O)-CH(Et)(n-Bu) | Et | H | H | fluorophenyl | H | *-(CH₂)₃-(CF₂)₃-CF₃ |
| 54 | *-(CH₂)₂-O-C(=O)-CH(Et)(n-Bu) | Et | H | H | thienyl | H | H |
| 55 | *-(CH₂)₂-O-C(=O)-CH(Et)(n-Bu) | *-(CH₂)₂-O-C(=O)-CH(Et)(n-Bu) | H | H | thienyl | H | *-(CH₂)₄-O-C(=O)-CH(Et)(n-Bu) |
| 56 | *-(CH₂)₂-O-Si(CH₃)₂-tBu | *-(CH₂)₂-O-Si(CH₃)₂-tBu | H | H | thienyl | H | n-Bu |
| 57 | *-(CH₂)₂-O-C(=O)-CH(Et)(n-Bu) | Et | *-O-CH₂-CH(Et)(n-Bu) | H | thienyl | H | *-(CH₂)₄-O-C(=O)-CH(Et)(n-Bu) |

-continued

| | | | | | | | |
|---|---|---|---|---|---|---|---|
| 58 | *—(CH₂)₂—O— C(=O)—CH(Et)(n-Bu) | Et | H | H | H | [thieno-dioxine, *,*] | H | *—(CH₂)₄—O—C(=O)—CH(CH₃)(CH₃) |
| 59 | *—(CH₂)₆—O— C(=O)—CH(Et)(n-Bu) | Et | H | CH₃ | H | [thieno-dioxine, *,*] | H | *—(CH₂)₂—O—C(=O)—CH(Et)(n-Bu) |
| 60 | *—(CH₂)₂—O— C(=O)—CH(Et)(n-Bu) | Et | H | *—O—CH(CH₃)(CH₃) | H | [thieno-dioxine, *,*] | H | *—CH(Et)(CH₂-n-Bu) (isobutyl-like) |
| 61 | *—(CH₂)₂—O— C(=O)—CH(Et)(n-Bu) | Et | H | H | H | thiophene-3,4-di(n-Hex) | H | *—(CH₂)₄—O—C(=O)—CH(CH₃)(CH₃) |
| 62 | *—(CH₂)₂—O— C(=O)—CH(Et)(n-Bu) | *—(CH₂)₂—O—C(=O)—CH(Et)(n-Bu) | H | CH₃ | H | thiophene-3,4-di(n-Hex) | H | H |
| 63 | *—(CH₂)₂—O— C(=O)—CH(Et)(n-Bu) | Et | H | CH₃ | H | thiophene-3,4-di(n-Hex) | H | *—(CH₂)₄—O—C(=O)—CH(Et)(n-Bu) |
| 64 | *—(CH₂)₂—O— C(=O)—CH(Et)(n-Bu) | Et | H | *—O—CH₂—CH(Et)(n-Bu) | H | thiophene-3,4-di(n-Hex) | H | n-Bu |

-continued

| | R₁ | R₂ | A₂ | R₁₁ | R₁₂ | R₃ |
|---|---|---|---|---|---|---|
| 69 | *–(CH₂)₂–O–C(O)–CH(Et)(n-Bu) | Et | phenyl | H | H | *–(CH₂)₄–O–C(O)–CH(CH₃)(CH₃) |
| 70 | *–(CH₂)₂–O–C(O)–CH(Et)(n-Bu) | Et | phenyl | n-Hex | n-Hex | n-Bu |
| 71 | *–(CH₂)₂–O–C(O)–CH(Et)(n-Bu) | Et | phenyl | n-Hex | n-Hex | *–(CH₂)₄–O–C(O)–CH(CH₃)(CH₃) |
| 72 | *–(CH₂)₂–O–C(O)–CH(Et)(n-Bu) | Et | phenyl | n-Hex | n-Hex | *–(CH₂)₃–(CF₂)₃–CF₃ |
| 73 | *–(CH₂)₆–O–C(O)–CH(Et)(n-Bu) | *–(CH₂)₂–O–C(O)–CH(Et)(n-Bu) | phenyl | n-Hex | n-Hex | *–(CH₂)₄–O–C(O)–CH(Et)(n-Bu) |
| 74 | *–CH(Et)(CH₂-n-Bu) | *–CH(Et)(CH₂-n-Bu) | phenyl | n-Bu | n-Bu | H |
| 75 | *–(CH₂)₂–O–C(O)–CH(Et)(n-Bu) | Et | phenyl | n-Bu | n-Bu | *–(CH₂)₄–O–C(O)–CH(Et)(n-Bu) |

-continued

| | | | | | |
|---|---|---|---|---|---|
| 76 | *―(CH₂)₂―O―C(O)―CH(Et)(n-Bu) | Et | phenyl | n-Bu | n-Bu |
| 77 | *―(CH₂)₂―O―C(O)―CH(Et)(n-Bu) | Et | phenyl | n-Bu | 1,3-dioxane |
| 78 | *―(CH₂)₂―O―C(O)―CH(Et)(n-Bu) | Et | phenyl | n-Bu | *―CH₂―C(O)―OCH₃ |
| 79 | *―(CH₂)₂―OCH₃ | Et | phenyl | n-Bu | *―(CH₂)₄―O―C(O)―CH(Et)(n-Bu) |
| 80 | *―(CH₂)₂―O―C(O)―CH(Et)(n-Bu) | Et | thienyl | H | *―(CH₂)₄―O―C(O)―CH(CH₃)₂ |
| 81 | *―(CH₂)₂―O―Si(CH₃)₂(tBu) | Et | thienyl | H | *―(CH₂)₄―O―C(O)―CH(CH₃)₂ |
| 82 | *―(CH₂)₂―O―C(O)―CH(Et)(n-Bu) | Et | thienyl | n-Hex | *―(CH₂)₄―O―C(O)―CH(CH₃)₂ |
| 83 | *―(CH₂)₂―O―C(O)―CH(Et)(n-Bu) | Et | thienyl | n-Hex | Et |

-continued

| | | | | |
|---|---|---|---|---|
| 84 | *—(CH₂)₂—O—Si(CH₃)₂—tBu | phenyl-thiazole | H, H | *—(CH₂)₂—O—Si(CH₃)₂—tBu | *—(CH₂)₄—O—C(O)—CH(Et)(n-Bu) |
| 85 | Et | phenyl-thiazole | H | *—(CH₂)₂—O—C(O)—CH(CH₃)(CH₃) | *—(CH₂)₄—O—C(O)—CH(CH₃)(CH₃) |
| 86 | Et | phenyl-thiazole | 1,3-dioxane | *—(CH₂)₂—O—C(O)—CH(CH₃)(CH₃) | *—(CH₂)₄—O—C(O)—CH(CH₃)(CH₃) |
| 87 | n-Hex | phenyl-thiazole | 1,3-dioxane | n-Hex | *—CH₂—C(O)—O—CH₂—CH(n-Bu)(Et) |
| 88 | Et | thiazole | H, H | *—(CH₂)₂—O—C(O)—CH(Et)(n-Bu) | *—(CH₂)₄—O—C(O)—CH(Et)(n-Bu) |
| 89 | Et | thiazole | H, H | *—(CH₂)₂—O—C(O)—CH(CH₃)(CH₃) | *—(CH₂)₄—O—C(O)—CH(CH₃)(CH₃) |

-continued

| | $R_1$ | $R_2$ | $A_2$ | $R_{11}$ | $R_{12}$ | $R_3$ |
|---|---|---|---|---|---|---|
| 90 | *–(CH$_2$)$_2$–O–C(=O)–CH(Et)(n-Bu) | Et | thiazole (*S, *N) | *–O–CH$_2$CH$_2$–O–* (1,3-dioxane) | | n-Bu |
| 91 | *–(CH$_2$)$_2$–O–C(=O)–CH(Et)(n-Bu) | Et | thiazole (*S, *N) | *–O–CH$_2$CH$_2$–O–* (1,3-dioxane) | | *–(CH$_2$)$_4$–O–C(=O)–CH(CH$_3$)$_2$ |
| 92 | *–(CH$_2$)$_2$–O–C(=O)–CH(Et)(n-Bu) | Et | pyrrole (NH) | n-Hex | n-Hex | *–(CH$_2$)$_4$–O–C(=O)–CH(CH$_3$)$_2$ |
| 93 | *–(CH$_2$)$_2$–O–C(=O)–CH(Et)(n-Bu) | Et | H$_3$C–CH$_2$–pyrrole (N-methylpyrrole) | H | H | n-Bu |

| | $R_1$ | $R_2$ | $A_2$ | $R_{11}$ | $R_{12}$ | $R_3$ |
|---|---|---|---|---|---|---|
| 94 | *–(CH$_2$)$_2$–O–C(=O)–CH(Et)(n-Bu) | Et | phenyl | n-Hex | n-Hex | n-Bu |
| 95 | *–(CH$_2$)$_2$–O–C(=O)–CH(Et)(n-Bu) | Et | phenyl | *–O–CH$_2$CH$_2$–O–* (1,3-dioxane) | | *–(CH$_2$)$_4$–O–C(=O)–CH(CH$_3$)$_2$ |

-continued

| | | | | | |
|---|---|---|---|---|---|
| 96 | *−(CH₂)₂−O−C(=O)−CH(Et)(n-Bu) | Et | thiophene (S, *,*) | H, H | *−(CH₂)₄−O−C(=O)−CH(CH₃)(CH₃) |
| 97 | *−(CH₂)₂−O−C(=O)−CH(Et)(n-Bu) | Et | thiophene (S, *,*) | n-Hex, n-Hex | *−(CH₂)₄−O−C(=O)−CH(CH₃)(CH₃) |
| 98 | *−(CH₂)₂−O−C(=O)−CH(Et)(n-Bu) | Et | thiophene (S, *,*) | n-Hex, n-Hex | *−CH₂−C(=O)−OCH₃ |
| 99 | *−(CH₂)₂−O−C(=O)−CH(Et)(n-Bu) | Et | thiophene (S, *,*) | 1,3-dioxane | *−(CH₂)₄−O−C(=O)−CH(CH₃)(CH₃) |
| 100 | *−(CH₂)₂−O−Si(CH₃)₂−tBu(CH₃) | *−(CH₂)₂−O−Si(CH₃)₂−tBu(CH₃) | thiophene (S, *,*) | 1,3-dioxane | n-Bu |
| 101 | *−(CH₂)₂−O−C(=O)−CH(Et)(n-Bu) | Et | 3,4-di(n-Hex)thiophene | n-Hex, n-Hex | *−(CH₂)₄−O−C(=O)−CH(CH₃)(CH₃) |
| 102 | *−(CH₂)₂−O−C(=O)−CH(Et)(n-Bu) | Et | 3,4-di(n-Hex)thiophene | n-Hex, n-Hex | n-Bu |
| 103 | *−(CH₂)₂−O−C(=O)−CH(Et)(n-Bu) | *−(CH₂)₂−O−C(=O)−CH(Et)(n-Bu) | 3,4-di(n-Hex)thiophene | n-Hex, n-Hex | *−(CH₂)₄−O−C(=O)−CH(CH₃)(CH₃) |

-continued

| | | | | | |
|---|---|---|---|---|---|
| 104 | *—(CH₂)₂—O— C(=O)—CH(Et)(n-Bu) | Et | *—S—(thiophene-3,4-diyl)—n-Hex, n-Hex | | *—(CH₂)₄—O—C(=O)—CH(CH₃)₂ (1,3-dioxolane) |
| 105 | *—(CH₂)₂—O—C(=O)—CH(Et)(n-Bu) | *—(CH₂)₂—O—C(=O)—CH(Et)(n-Bu) | *—S—(thiophene-3,4-diyl)—n-Hex, n-Hex | | n-Bu (1,3-dioxolane) |
| 106 | *—(CH₂)₂—O—C(=O)—CH(Et)(n-Bu) | Et | 4-phenylthiazol-2,5-diyl | H, H | *—(CH₂)₄—O—C(=O)—CH(CH₃)₂ |
| 107 | *—(CH₂)₂—O—C(=O)—CH(Et)(n-Bu) | *—(CH₂)₂—O—C(=O)—CH(Et)(n-Bu) | 4-phenylthiazol-2,5-diyl | H, H | n-Bu |
| 108 | *—(CH₂)₂—O—C(=O)—CH(Et)(n-Bu) | Et | 4-phenylthiazol-2,5-diyl | n-Hex, n-Hex | *—(CH₂)₄—O—C(=O)—CH(CH₃)₂ |
| 109 | *—(CH₂)₂—O—C(=O)—CH(Et)(n-Bu) | Et | 4-phenylthiazol-2,5-diyl | | *—(CH₂)₄—O—C(=O)—CH(CH₃)₂ (1,3-dioxolane) |

-continued
| | | | | | | |
|---|---|---|---|---|---|---|
| 110 | *-(CH₂)₆-O-C(=O)-CH(Et)(n-Bu) | *-(CH₂)₆-O-C(=O)-CH(Et)(n-Bu) | 4-phenyl-thiazolyl | H | n-Bu | |
| 111 | *-(CH₂)₂-O-C(=O)-CH(Et)(n-Bu) | Et | thiazolyl | H | H | |
| 112 | *-(CH₂)₂-O-C(=O)-CH(Et)(n-Bu) | Et | thiazolyl | n-Hex | n-Hex | *-(CH₂)₄-O-C(=O)-CH(CH₃)₂ |
| 113 | *-CH(Et)(CH₂-n-Bu) | *-CH(Et)(CH₂-n-Bu) | thiazolyl | n-Hex | n-Hex | *-(CH₂)₄-O-C(=O)-CH(CH₃)₂ |
| R₁ | R₂ | A₂ | R₁₁ | R₁₂ | R₃ |
|---|---|---|---|---|---|
| 114 | *-(CH₂)₂-O-C(=O)-CH(Et)(n-Bu) | Et | thienyl | H | H | *-(CH₂)₄-O-C(=O)-CH(CH₃)₂ |

-continued

| No. | R₁ | R₂ | Ring | R₃ | R₄ | R₅ |
|---|---|---|---|---|---|---|
| 115 | n-Hex | *–(CH₂)₂–O–C(O)–CH(Et)(n-Bu) | thiophene (2,5-linked) | H | H | *–(CH₂)₄–O–C(O)–CH(CH₃)₂ |
| 116 | Et | *–(CH₂)₂–O–C(O)–CH(Et)(n-Bu) | thiophene (2,5-linked) | n-Hex | n-Hex | *–(CH₂)₄–O–C(O)–CH(CH₃)₂ |
| 117 | Et | *–(CH₂)₂–O–C(O)–CH(Et)(n-Bu) | thiophene (2,5-linked) | n-Hex | n-Hex | *–(CH₂)₄–O–C(O)–CH(CH₃)₂ |
| 118 | Et | *–(CH₂)₂–O–C(O)–CH(Et)(n-Bu) | thiophene (2,5-linked) | n-Hex | n-Hex | n-Bu |
| 119 | n-Hex | *–(CH₂)₂–O–C(O)–CH(Et)(n-Bu) | thiophene (2,5-linked) | CN | (phenyl) | *–(CH₂)₄–O–C(O)–CH(CH₃)₂ |
| 120 | Et | n-Hex | thiophene (2,5-linked) |  | (1,3-dioxolan-2,2-diyl) | H |
| 121 | Et | *–(CH₂)₂–O–C(O)–CH(Et)(n-Bu) | 3,4-di(n-Hex)-thiophene (2,5-linked) | H | H | H |
| 122 | Et | *–(CH₂)₂–O–C(O)–CH(Et)(n-Bu) | 3,4-di(n-Hex)-thiophene (2,5-linked) | n-Hex | n-Hex | *–(CH₂)₄–O–C(O)–CH(CH₃)₂ |

-continued

| | | | | | | |
|---|---|---|---|---|---|---|
| 123 | *−(CH₂)₂−O−C(=O)−CH(Et)(n-Bu) | thiophene with n-Hex, n-Hex | n-Hex | n-Hex | Et | *−(CH₂)₄−O−C(=O)−CH(Et)(n-Bu) |
| 124 | *−(CH₂)₂−O−C(=O)−CH(Et)(n-Bu) | thiophene with n-Hex, n-Hex | CN | phenyl | Et | *−(CH₂)₄−O−C(=O)−CH(CH₃)₂ |
| 125 | *−(CH₂)₂−O−C(=O)−CH(Et)(n-Bu) | thiophene with n-Hex, n-Hex | | 1,3-dioxane | Et | *−(CH₂)₄−O−C(=O)−CH(CH₃)₂ |
| 126 | *−(CH₂)₂−O−Si(CH₃)₂−tBu | thiophene with n-Hex, n-Hex | | 1,3-dioxane | *−(CH₂)₂−O−Si(CH₃)₂−tBu | *−CH₂−O−C(=O)−CH(n-Bu)(Et) |
| 127 | *−(CH₂)₂−O−C(=O)−CH(Et)(n-Bu) | thiazole-phenyl | | H | Et | *−(CH₂)₄−O−C(=O)−CH(CH₃)₂ |
| 128 | *−(CH₂)₂−O−C(=O)−CH(Et)(n-Bu) | thiazole-phenyl | | H | *−(CH₂)₂−O−C(=O)−CH(Et)(n-Bu) | H |

-continued

| | | | | | |
|---|---|---|---|---|---|
| 129 | *—(CH₂)₂—O | n-Bu | thiazolyl-phenyl | n-Hex | n-Hex | *—(CH₂)₄—O—C(O)—CH(CH₃)₂ |
| 130 | *—(CH₂)₂—O—C(O)—CH(Et)(n-Bu) | Et | thiazolyl-phenyl | n-Hex | n-Hex | n-Bu |
| 131 | *—(CH₂)₂—O—C(O)—CH(Et)(n-Bu) | Et | thiazolyl-phenyl | 1,3-dioxolane | H | *—(CH₂)₄—O—C(O)—CH(CH₃)₂ |
| 132 | *—(CH₂)₂—O—C(O)—CH(Et)(n-Bu) | Et | thiazolyl | H | H | *—(CH₂)₄—O—C(O)—CH(CH₃)₂ |

| | | | | | |
|---|---|---|---|---|---|
| 133 | *─(CH₂)₂─O─C(=O)─CH(Et)(n-Bu) | Et | ![thiazole]* | n-Hex | n-Hex | *─(CH₂)₄─O─C(=O)─CH(CH₃)₂ |
| 134 | *─(CH₂)₂─O─C(=O)─CH(Et)(n-Bu) | Et | ![thiazole]* | CN | Ph | H |
| 135 | *─(CH₂)₂─O─Si(CH₃)₂─tBu | *─(CH₂)₂─O─Si(CH₃)₂─tBu | ![4-methylthiazole]* | n-Hex | n-Hex | *─(CH₂)₄─O─C(=O)─CH(CH₃)₂ |

(136)

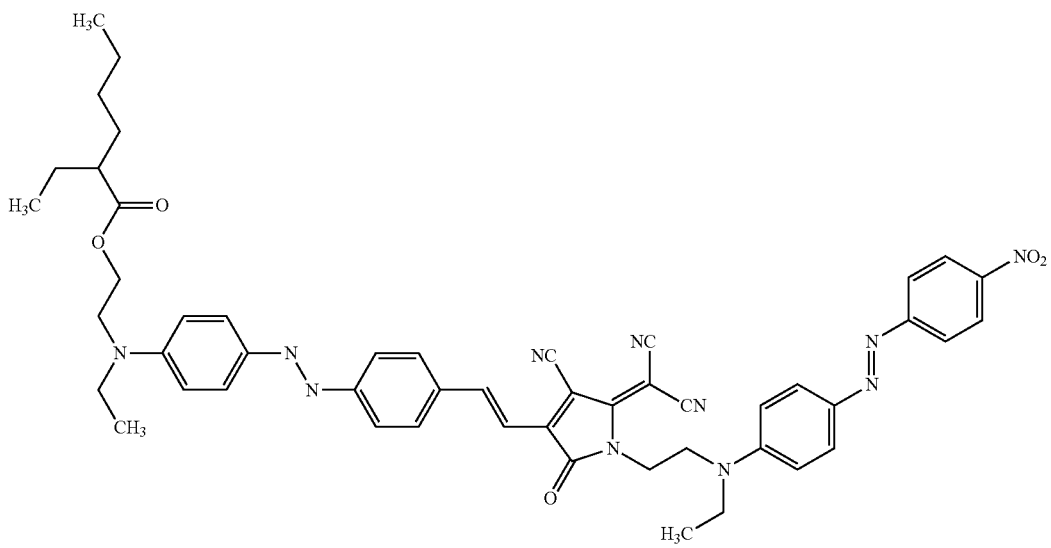

In the above table, Et represents an ethyl group, n-Bu represents a normal butyl group, n-Hex represents a normal hexyl group, t-Bu represents tertiary butyl group, and the asterisk represents the binding site. Further, the substituent group of $A_2$ in the table may be either bonded in the exactly described direction or may be bonded in the direction of the reversed left to right.

Hereinafter, the synthesis of the organic compound having a nonlinear optical activity used in the present invention will be described. The organic compound having a nonlinear optical activity used in the present invention is primarily preferably to use a synthesis described below.

—Suzuki-Miyaura Coupling Reaction of a Compound Represented by the Following Formula (1) with a Compound Represented by the Following Formula (2)—

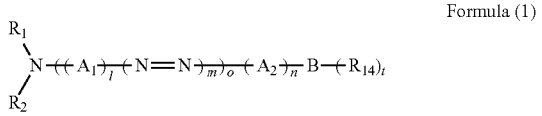

Formula (1)

($R_1$, $R_2$, $A_1$, $A_2$, l, m and o in Formula (I) have the same meanings as $R_1$, $R_2$, $A_1$, $A_2$, l, m and o in Formula (II). n represents an integer of 1 to 3, $R_{14}$ represents an alkoxy group, a hydroxy group or a halogen atom, t represents an integer of 2 or 3. When t is 3, since the valence of B becomes −1, there is a corresponding monovalent cation. If $R_{14}$ is an alkoxy group, they may be bonded to each other to form a ring.

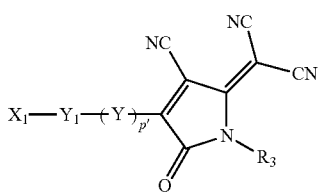

Formula (2)

($R_3$ and Y in Formula (2) have the same meanings as $R_3$ and Y in Formula (II). $X_1$ represents a chlorine atom, a bromine atom or an iodine atom, $Y_1$ represents a substituted or unsubstituted aromatic group, and p' represents an integer of 0 to 2.)

The monovalent cation present in the case when t in Formula (1) is 3 includes a potassium ion ($K^+$) or sodium ion ($Na^+$), and the like.

Suzuki-Miyaura coupling reaction may be carried out with reference to the description of "Chemical Reviews (Chem. Rev.), 95, (1995), pp. 2457-2483."

The synthesis, for example, may be particularly preferably applied to the synthesis of the compound represented by Formulas (III) and (IV).

The compound represented by Formula (III) may be synthesized by Suzuki-Miyaura coupling reaction of the compound represented by Formula (3) with the compound represented by Formula (4).

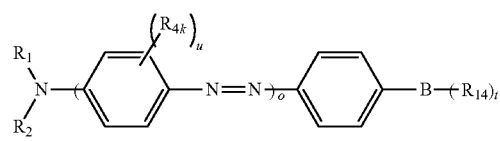

Formula (3)

(In Formula (3), $R_1$, $R_2$, and o have the same meaning as $R_1$, $R_2$, and o in Formula (III). $R_{14}$ and t have the same meaning as $R_{14}$ and t in Formula (1). $R_{4k}$ represents a hydrogen atom, a substituted or unsubstituted alkyl group, a substituted or unsubstituted aryl group, a substituted or unsubstituted heteroaryl group, a substituted or unsubstituted alkoxy group, a substituted or unsubstituted alkylthio group, a substituted carbamoyl group or a substituted or unsubstituted acylamino group, u represents an integer of 1 to 4, and each $R_{4k}$ may be the same or different.)

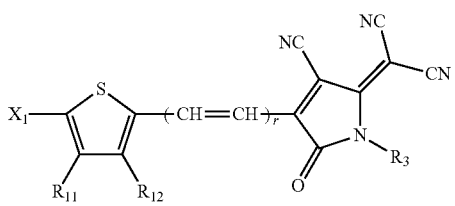

Formula (4)

(In Formula (4), $R_3$, $R_{11}$, $R_{12}$ and r have the same meaning as $R_3$, $R_{11}$, $R_{12}$ and r in Formula (III). $X_1$ has the same meaning as $X_1$ in Formula (2).)

In the coupling reaction of the compound represented by Formula (3) with the compound represented by Formula (4), for example, a palladium catalyst, such as bis(diphenylphosphino)ferrocene) palladium dichloride $CH_2Cl_2$ complex, a phosphorus ligand such as 2-(di-t-butylphosphino)biphenyl, and a base such as a potassium carbonate or a potassium phosphate may be suitably used.

Since the compound represented by Formula (4) tends to be easily decomposed under basic conditions, it should be noted that the reaction conditions have. The reaction solvent preferably uses an ether-based solvent such as 1,2-dimethoxyethane containing no basicity or a hydrocarbon-based solvent such as toluene. Further, in the case of using a compound wherein Formula (1) or (3), t represents 3 and $R_{14}$ represents a cyclic alkoxy group, the compound may be synthesized without using a base as mentioned above.

The compound represented by Formula (3), for example, may be synthesized with reference to the method described in "Organic Letters (Org. Lett.)", 3, (2001), pp. 3891-3893, and the compound represented by Formula (4), for example, may be synthesized with reference to "Journal of Organic chemistry (J. Org. Chem.)", 71, (2006), pp. 6734-6741 and the U.S. Pat. No. 3,013,013.

—A Synthesis of the Compound Represented by the Following Formula (5), Mitsunobu Reaction of an Alcohol with the Compound Represented by the Following Formula (6)—

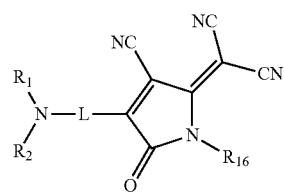

Formula (5)

In Formula (5), $R_1$, $R_2$ and L have the same meaning as $R_1$, $R_2$ and L in Formula (I). $R_{16}$ represents a substituted or unsubstituted alkyl group or a substituted or unsubstituted aryl group.

$R_{16}$ includes the same as those mentioned in a substituted or unsubstituted alkyl group, a substituted or unsubstituted aryl group that $R_3$ in Formula (III) represented, and the preferred groups are also the same.

The compound of Formula (5) may be synthesized by Mitsunobu reaction of an alcohol represented by Formula "$R_{16}$—OH" with the compound represented by the following Formula (6).

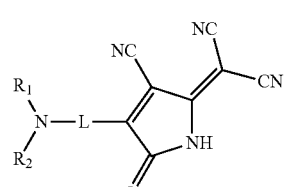

Formula (6)

In Formula (6), $R_1$, $R_2$ and L have the same meaning as $R_1$, $R_2$ and L in Formula (I).

Mitsunobu reaction may be carried out with reference to the description of "Synthesis", 1, (1981), pp. 1-28.

The synthesis may be preferably applied to, for example, the synthesis of compound represented by the following Formula (7).

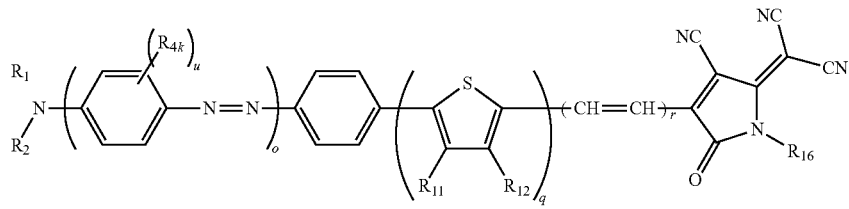

Formula (7)

(In Formula (7), $R_1$, $R_2$, $R_{11}$, $R_{12}$, o, q, and r have the same meaning as $R_1$, $R_2$, $R_{11}$, $R_{12}$, o, q, and r in Formula (III). $R_{4k}$ and u have the same meaning as $R_{4k}$ and u in Formula (3). $R_{16}$ has the same meaning as $R_{16}$ in Formula (5).)

The compound represented by Formula (7) may be synthesized by Mitsunobu reaction of the compound represented by the following Formula (8) with an alcohol represented by Formula "$R_{16}$—OH".

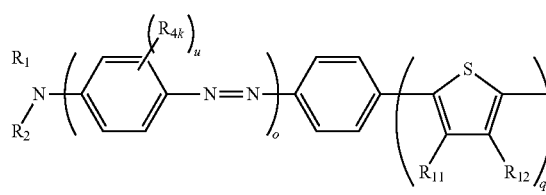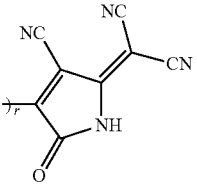

Formula (8)

(In Formula (8), $R_1$, $R_2$, $R_{11}$, $R_{12}$, o, q, and r have the same meaning as $R_1$, $R_2$, $R_{11}$, $R_{12}$, o, q, and r in Formula (III). $R_{4k}$ and u have the same meaning as $R_{4k}$ and u in Formula (3).)

As the catalyst for the Mitsunobu reaction of alcohols with the compound represented by Formula (8), for example, azodicarboxylic acid esters such as diethyl azodicarboxylate and phosphines such as triphenylphosphine are preferably used.

As the alcohols represented by Formula "$R_{16}$—OH", primary or secondary alcohols are preferred.

A similar alkylation reaction, for example, is described in "Chemistry of Materials (Chem. Mater.)", 18, (2006), pp. 2982-2988, but since the solubility of the substrate to acetonitrile as a solvent is low, there was no reproducibility. In addition, there are cases that the highly soluble N,N-dimethylformamide was used as a solvent (for example, "Journal of Polymer Science: Part A: Polymer Chemistry (J. Polym. Sci. Part A)", 4542007), pp. 531-542), but they had a problem that the yield is low. Since the reaction according to the invention may be carried out under the mild conditions, it becomes possible to obtain a desired product in high yield. The same reaction may be particularly preferably used in the case of the compound of r=1 in Formulas (7) and (8).

The compound that q in Formula (8) represents 1 may be preferably synthesized by using the aforementioned Suzuki-Miyaura coupling reaction, and the compound that q represents 1 may preferably use the same method as the synthesis of a compound represented by Formula (V) set forth below.

The compound represented by Formula (V) may be preferably synthesized by using an intermediate represented by the following Formula (9).

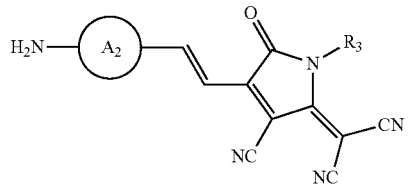

Formula (9)

(In Formula (9), $R_3$ and $A_2$ have the same meaning as $R_3$ and $A_2$ in Formula (V).)

The compound represented by Formula (9), for example, may be synthesized with reference to the method described in U.S. Pat. No. 7,307,173.

The compound represented by Formula (V) may be synthesized by diazotizing the intermediate represented by Formula (9) and subsequently carrying out an azo coupling reaction with the corresponding substrate. Diazotization of the intermediate (9) is preferably carried out by using a diazotizing agent such as nitrosyl sulfate in a strong acid such as 85% phosphoric acid aqueous solution. Azo coupling reaction may be carried out with reference to "New Experimental Chemistry Course 14, Synthesis and Reaction of Organic Compound [III], p. 1525".

The detailed embodiments of the reaction are described in the Example set force below.

The sublimation temperature of the organic compound having a nonlinear optical activity used in the present invention described above is preferably 130° C. or more, and more preferably 170° C. or more.

Further, the organic compound having a nonlinear optical activity used in the present invention, as described above, is required to be excellent in solubility in a solvent of the coating solution in manufacturing the organic nonlinear optical material. The corresponding solubility, for example, may be preferably dissolved 1% by mass or more and more preferably 5% by mass or more at room temperature to the solvent such as tetrahydrofuran, cyclopentanone, chloroform, N,N-dimethylacetamide and the like.

In addition, since the electro-optic constant of the organic compound having a nonlinear optical activity used in the present invention is mainly proportional to the hyperpolarization ratio $\beta_0$ in the electrostatic field of the organic compound having a nonlinear optically active, $\beta_0$ is preferably $150 \times 10^{-30}$ D·esu or more, and more preferably $200 \times 10^{-30}$ D·esu or more. Further, the above mentioned $\beta_0$ may be estimated by commercial simulation software for calculating molecular orbital, and the electro-optical constant may be measured by a measuring method such as a normal. ATR method, reflection method of ellipsometry, or the like.

In the organic nonlinear optical material of the present invention, since the content of the organic compound having a nonlinear optical activity is different depending on the required nonlinear optical performance, mechanical strength, or the kind of the used organic compound having a nonlinear optical activity, and the like, it may not be uniformly defined, but in general, it is preferably in the range of 1 to 90% by mass as the ratio of the total mass of the organic nonlinear optical material. The reason is, if it is less than 1% by mass, there are many case of not obtaining a sufficient nonlinear optical performance, or if it exceeds 90% by mass, there is a tendency that the problem of not obtaining sufficient mechanical strength occurs. The more preferred content of the organic compound having a nonlinear optical activity is preferably in the range of 5 to 75% by mass, and more preferably in the range of 10 to 60% by mass.

Further, the preferred content of the organic compound having the nonlinear optical activity is in the same range in the case that the organic compound having a nonlinear optical activity is dispersed in a polymer binder or bound to a polymer binder.

<Polymer Binder>

The polymer binder used in the present invention may be any one as long as it has excellent optical quality and film-forming property, but the glass transition temperature is preferably 130° C. or more from the viewpoint of suppressing the orientation relaxation of the organic compound having the nonlinear optical activity. Particularly preferably, it is the one whose glass transition temperature is 140° C. or more, and the mechanical strength is high. Specifically, it includes polycarbonate, polyimide, polyarylate, plycyclic olefins, polycyanurate, polyester, acrylic polymers, epoxy polymers in particular and the like. Further, it may be a mixture or a copolymer of two or more of these plural polymers.

Further, in the present invention, the measurement of the glass transition temperature of the organic nonlinear optical material described later and the above mentioned polymer binder is carried out by using a differential scanning calorimeter (DSC), and the temperature corresponding to the intersection of the base line and the slope of the rising portion of the endothermic process according to the glass transition when measuring at a heating rate of 10° C. per minute from the room temperature is set to be a glass transition temperature.

In the organic nonlinear optical material of the present invention, the content ratio of the polymer binder and the organic compound having the nonlinear optical activity is preferably from 1/99 to 90/10, and more preferably from 5/95 to 60/40.

<Other Components>

The organic nonlinear optical material of the present invention may have, in addition to the polymeric binder and organic compound having a nonlinear optical activity, if necessary, the addition of various types of additives. For example, on the purpose of preventing oxidative deterioration of the organic compound having a nonlinear optical activity and/or the polymer binder, the known antioxidants such as 2,6-di-t-butyl-4-methyl phenol, hydroquinone, or on the purpose of preventing ultraviolet deterioration of the organic compound having a nonlinear optical activity or the polymer binder, the known UV absorbers such as 2,4-dihydroxy benzophenone, 2-hydroxy-4-methoxy benzophenone may be used. Further, the inorganic fine particles (e.g., zirconium oxide, titanium oxide, zinc sulfide, etc.) as a refractive index controlling agent for improving the performance as an optical device, or the organic compound having a high refractive index (e.g., diphenyl sulfide, diphenyl, diphenyl sulfoxide, etc.) may be used.

When adding the above mentioned additives, the content ratio of the polymer binder containing an organic compound having a nonlinear optical activity consisting of the above mentioned preferred content ratio is preferably 1 to 99 parts by weight, the content of the additive is preferably 1 to 99 parts by weight, and the content ratio of the polymer binder containing an organic compound having a nonlinear optical activity is more preferably 5 to 90 parts by weight, and the content of the additive is more preferably 5 to 90 parts by weight.

Further, when manufacturing an organic nonlinear optical material by a wet coating, on the purpose of improving the surface smoothness of the coating film, the known leveling agents such as silicone oil or in the case of using an organic compound having a nonlinear optical activity having a crosslinked curable functional group and/or a polymer binder, and the known curing catalysts or curing aids on the purpose of promoting the crosslinking and curing may be added to the coating liquid.

<Organic Nonlinear Optical Material>

The form of an organic nonlinear optical material of the present invention may be any one, but it is generally used in the form of a thin film for the application to nonlinear optical device. As a manufacturing method of the thin film containing an organic nonlinear optical material of the present invention, a known method such as injection molding, press molding, soft lithography method, a wet coating method or the like is available, but from the viewpoint of the ease, mass production, film quality (the small defects such as the uniformity of film thickness, air bubbles, etc.) or the like of the manufacturing equipment, a wet coating method which applies a solution prepared by dissolving a polymer binder and an organic compound having at least the nonlinear optical activity in an organic solvent on an appropriate substrate to form film by methods such as a spin coating method, a blade coating method, a dip coating method, an ink jet method, a spraying method, and the like is preferred.

The organic solvents used in the wet coating process may be any one as long as they may dissolve a polymer binder and an organic compound having an available nonlinear optical activity, but the solvent whose boiling point is in the range of 80° C. to 200° C. is preferred. If an organic solvent whose boiling point is less than 80° C. is used, there is a tendency of the problem that the solvent volatilization occurs and the viscosity of the coating solution changes (increases) during storage of the coating solution or the volatilization rate of the solvent is too fast and thus condensation occurs becomes significant. Meanwhile, if an organic solvent whose boiling point is more than 200° C. is used, there might be problems that the solvent removal after coating becomes difficult and the remaining organic solvent functions as a plasticizer for the polymer binder to result in a decrease of the glass transition temperature.

Examples of suitable organic solvents include diethyleneglycoldimethylether, cyclopentanone, cyclohexanone, cyclohexanol, toluene, chlorobenzene, xylene, N,N-dimethylformamide, N,N-dimethylacetamide, dimethylsulfoxide, 2,2,3,3-tetrafluoro-1-propanol, 1,2-dichloroethane, 1,2-dichloropropane, 1,3-dichloropropane, 1,2,3-trichloropropane, or the like. In addition, these organic solvents may be used alone or as a mixture of plurality thereof. Further, a mixed solvent which adds an organic solvent such as tetrahydrofuran, methylethylketone, isopropanol, chloroform, or the like whose boiling point is less than 80° C. to these desirable organic solvents is also available.

The organic nonlinear optical material of the present invention may be fabricated by using the coating solution prepared in the above manner, for example, by forming a thin film by the above mentioned spin coating method, or the like. As described above, a polymer binder whose glass transition temperature is relatively high in the present invention may be used, but as the prepared organic nonlinear optical material comprising an organic compound having a nonlinear optical activity, the one whose glass transition temperature is high is preferred from the viewpoint of heat resistance or the like.

Thus, the glass transition temperature of the organic nonlinear optical materials is preferably 100° C. or more, and more preferably 150° C. or more.

In order to generate the secondary nonlinear optical activity in the nonlinear optical materials polymeric system, as described above, it is necessary to orient the organic compound having a nonlinear optical activity. As an orientation method for this, there is a method of applying a nonlinear optical material of polymeric system on a substrate having an orientation film on its surface and of inducing an orientation of the organic compound having a nonlinear optical activity in the nonlinear optical material of the polymeric system by the orientation property of the orientation film. In addition, the known poling method such as a light poling method, a laser-assisted electric field poling method, an electric field poling method may be also effectively used. Among these, an electric field poling method is particularly preferred in terms of simplicity of the device, high degree of the obtained orientation, or the like.

The electric field poling method may be roughly divided into a contact poling method for applying an electric field by interposing the nonlinear optical material between a pair of electrodes and a corona poling method for conducting corona discharge on the surface of the nonlinear optical material of the substrate electrode and applying a charging electric field. The electric field poling method is an orientation method that orientates (poling) the nonlinear optically active compound in the direction of the applied electric field by the Coulomb force with the applied electric field and the dipole moment of the nonlinear optically active compound.

In the electric field poling method, in general, the sufficient orientation is induced by heating to a temperature near the glass transition temperature of the nonlinear optical material to facilitate the orientation movement in the electric field direction of the nonlinear optically active compound at the state of applying an electric field. Then, at the state of applying an electric field, the orientation state is frozen by cooling to the room temperature to remove the applied electric field.

However, since this orientation state is basically in a thermodynamic non-equilibrium state, there is a fundamental problem that is gradually randomized over time even at a temperature below the glass transition temperature and nonlinear optical activity becomes lowered.

Since the randomization of the orientation state by the lapse of time develops slowly depending on how large the difference between the glass transition temperature and ambient temperature where the nonlinear optical material is placed in is, this problem may be substantially solved by designing the glass transition of the nonlinear optical material high by using a binder resin having a high glass transition temperature in actual use. In the present invention, a polymer binder whose glass transition temperature is 130° C. or more may be preferably used, but even in this case, the sublimation temperature of the organic compound having a nonlinear optical activity used in the present invention is high. Thus, a nonlinear optical material having an excellent stability or nonlinear optical performance may be produced without being sublimed or deteriorated when heating.

As an indicator to determine if it was poling, there is a numerical value (order parameter: $\phi$) indicating whether any amount of the nonlinear optical molecules (generally having dichroism) is oriented in the direction of the electric field. In particular, if the absorbance when the molecular orientation becomes random is set to $A_0$, and if the absorbance when the molecule is oriented in the direction of the electric field (film thickness direction) is set to $A_f$, $\phi$ is intended to be calculated by $1-(A_f/A_0)$.

The order parameter indicates 1 in an ideal state that all molecules are completely oriented, and 0 when it is completely random. It represents that the higher the value is, the greater the degree of orientation of the molecule is as a whole. By measuring this value, how much efficiently it was poling may be determined, and its stability may be also evaluated.

<Optical Device>

The optical device of the present invention is characterized in making use of organic nonlinear optical material of the present invention and it may be any one as long as it operates based on the nonlinear optical effect, and specific examples thereof, for example, include a wavelength conversion device, a photorefractive device, an electro-optical device, and the like. Particularly preferably, it may be the electro-optical device such as an optical switch, an optical modulator, a phase shifter or the like operating on the basis of the electro-optic effect.

As the above mentioned electro-optical device, a device having a structure for forming a nonlinear optical material on a substrate and for inserting a pair of electrode for the input electrical signal may be preferably used.

As a material constituting such a substrate, metal such as aluminum, gold, iron, nickel, chromium, titanium and the like; a semiconductor such as silicon, titanium oxide, zinc oxide, gallium-arsenic and the like; glass; plastic such as polyethylene terephthalate, polyethylene naphthalate, polycarbonate, polysulfone, polyether ketone, polyimide and the like may be used.

On the surface of these substrate materials, a conductive film may be formed, and as the material for the corresponding conductive film, metal such as aluminum, gold, nickel, chromium, and titanium; a conductive oxide such as tin oxide, indium oxide, ITO (tin oxide-indium oxide composite oxide), IZO (indium oxide-zinc oxide composite oxide) and the like; a conductive polymer such as polythiophene, polyaniline, polyparaphenylene vinylene, polyacetylene and the like may be used. Such a conductive film may be formed by using a known dry film forming method such as deposition, sputtering and the like, or a known wet film forming method such as dip coating, electrolytic precipitation and the like, and if necessary patterns may be formed. Further, a conductive substrate or a conductive film formed on a substrate as described above may be used as an electrode (hereinafter, referred to as "lower electrode") during poling or operation of the device.

Furthermore, if necessary, an adhesive layer for improving the adhesion between the substrate and the film formed thereon, a leveling layer for smoothing the irregularities of the substrate surface, or any intermediate layer for providing collectively these functions may be formed on the substrate surface. A material for forming such a film is not particularly limited, but for example, acrylic resins, methacrylic resins, amide resins, vinyl chloride resins, vinyl acetate resins, phenol resins, urethane resins, vinyl alcohol resins, acetal resin, and copolymer thereof; a crosslinked product such as zirconium chelate compounds, titanium chelate compounds, silane coupling agents and co-crosslinking thereof; and the like may be used.

The electro-optical device, a nonlinear optical device of the present invention may be preferably formed as including waveguide structure, and a nonlinear optical material of the present invention may be particularly preferably contained in the core layer of the waveguide.

A cladding layer (hereinafter, referred to as "lower cladding layer") may be formed between the substrate and the core layer containing a nonlinear optical material of the present invention. A lower clad layer may be any one whose refractive index is lower than that of the core layer as long as it is not corroded during forming a core layer. As such, UV-curable or thermosetting resin such as acrylic resin, epoxy resin, oxetane resin, thiirane resin, silicone resin; polyimide; glass or the like are preferably used.

After forming a core layer by a nonlinear optical material of the present invention, a clad layer (hereinafter, referred to as "upper cladding layer") may be also formed on its upper portion in the same manner as the lower cladding layer. As a result, the slab waveguide consisting of a substrate/a lower cladding layer/a core layer/an upper cladding layer may be formed.

After forming a core layer, the core layer may be patterned by a known method using a semiconductor process technology such as reactive ion etching (RIE), photolithography, electron beam lithography or the like to form a channel waveguide or a ridge waveguide. Alternatively, a channel-type waveguide may be formed by patterning and irradiating UV light, electron beams or the like to a part of the core layer, and by changing the refractive index of the irradiated portion.

A basic electro-optical device may be formed by forming electrodes (hereinafter, referred to as "upper electrode") for applying an input electrical signal to a surface of the upper cladding layer in a desired region of the upper cladding layer.

When forming the ridge waveguide or the channel waveguide in the manner described above, the known device structure such as linear type, Y-branch type, a directional coupler type, Mach-Zehnder type, etc. may be configured as the pattern of the core layer, and applied to the known optical information communication devices such as optical switches, optical modulators, a phase shifter or the like.

EXAMPLE

Hereinafter, examples of the present invention will be described, but the present invention is not intended to be limited to these examples. "%" and "parts" as the content of the examples both are based on mass.

Synthesis Example 1

Synthesis of Exemplary Compound (1)

Exemplary Compound (1) was synthesized according to the following scheme.

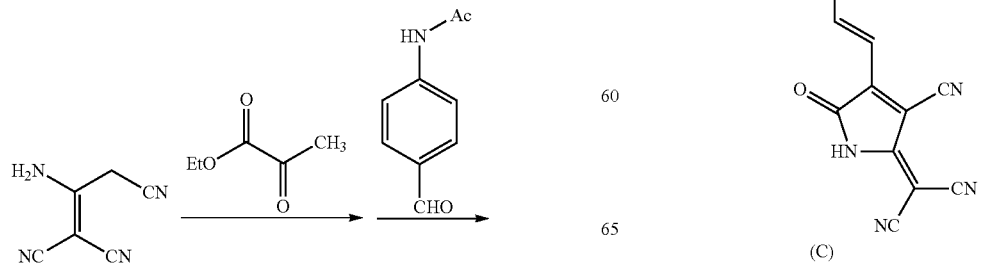

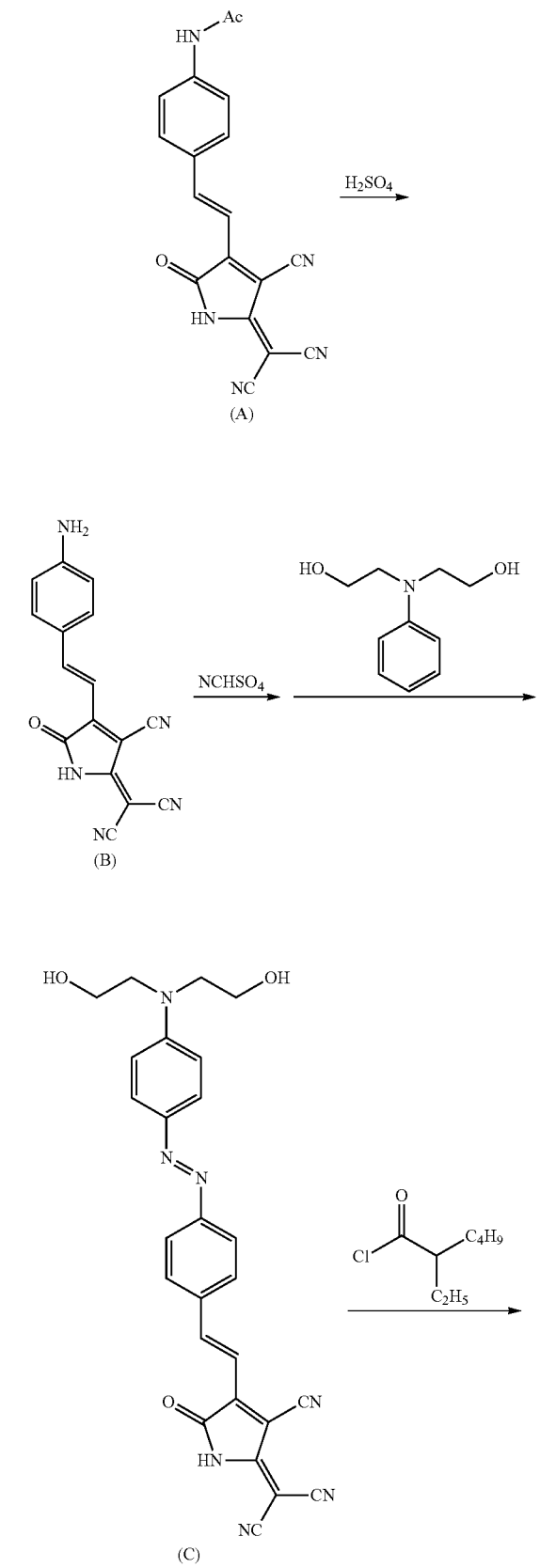

-continued

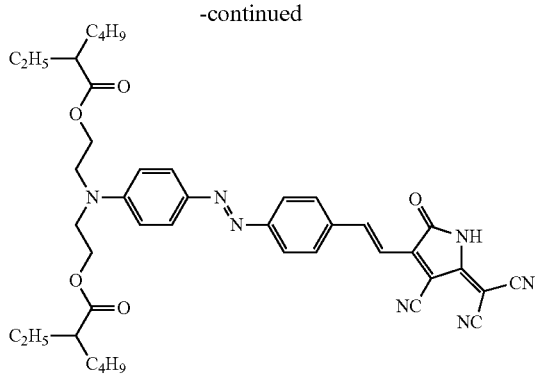

—Synthesis of Intermediate (A)—

350 ml of ethanol was added to 15.5 g (0.12 mol) of 2-amino-1,1,3-tricyano-1-propene and 27.3 g (0.24 mol) of ethyl pyruvate, and heated to reflux for 1 hour under nitrogen flow. After cooling, solution of 15.3 g (0.094 mol) of 4-acetamide benzaldehyde dissolved in 50 ml of 2-methoxyethanol was added to the reaction solution, and heated to reflux for 2 hours under nitrogen flow. After cooling to room temperature, the precipitated crystals were separated by filtration to yield 16.2 g (52% yield) of an intermediate (A).

—Synthesis of Intermediate (B)—

350 ml of ethanol was added to 15.0 g (0.046 mol) of the resulting intermediate (A), and heated to reflux, and 15 ml of the concentrated sulfuric acid was carefully added dropwise to the solution. Until the intermediate (A) was consumed, the concentrated sulfuric acid was added as appropriate, and continued to heat to reflux. After cooling, the crystals were separated by filtration to yield 10 g (76% yield) of an intermediate (B).

—Synthesis of Intermediate (C)—

21 ml of aqueous solution of phosphoric acid (85% concentration) was added to 3 g (0.010 mol) of the intermediate (B), and stirred for 30 minutes under being ice-cooled. 4 g (0.013 mol) of 40% nitrosyl sulfate solution was carefully added dropwise while being ice-cooled not to generate heat in excess, and stirred further for 1 hour to give diazonium salt solution of the intermediate (B). The previously prepared diazonium solution was added to the solution of 3.8 g (0.021 mol) of N-phenyethanolamine dissolved in 200 ml of methanol under being ice-cooled. After being stirred for 2 hours, the crystals were separated by filtration to yield 1.9 g (yield 38%) of an intermediate (C).

—Synthesis of Exemplary Compound (1)—

1.5 g (0.0031 mol) of the intermediate (C) was dissolved in 15 ml of N,N-dimethylacetamide, and heated to 50° C. 0.59 g (0.0075 mol) of pyridine and 1.2 g (0.0074 mol) of 2-ethylhexanoyl chloride was added dropwise thereto, and heated and stirred at 50° C. for 4 hours. After cooling to room temperature, liquid separation operation was carried out by adding 150 ml of ethyl acetate and 150 ml of water to the reaction solution. The reactants were dehydrated over magnesium sulfate and separated by filtration, and the solvent of the organic layer was distilled off under reduced pressure. The resulting solid was purified by silica gel column chromatography (chloroform/methanol=10/1) to give Exemplary Compound (1). The quantity was 1.0 g, and the yield was 44%.

$^1$H NMR (CDCl$_3$) δ 8.68 (br, 1H), 8.50 (d, 1H), 7.91 (d, 2H), 7.89 (d, 2H), 7.78 (d, 2H), 7.21 (d, 1H), 6.91 (d, 2H), 4.34 (t, 4H), 3.75 (t, 4H), 2.28 (m, 2H), 1.40-1.68 (m, 8H), 1.15-1.37 (m, 8H), 0.86 (m, 12H) ppm UV-Vis spectrum: $\lambda_{max}$=621 nm (chloroform solution)

Synthesis Example 2

Preparation of Exemplary Compound (2)

Exemplary Compound (2) was synthesized according to the following scheme.

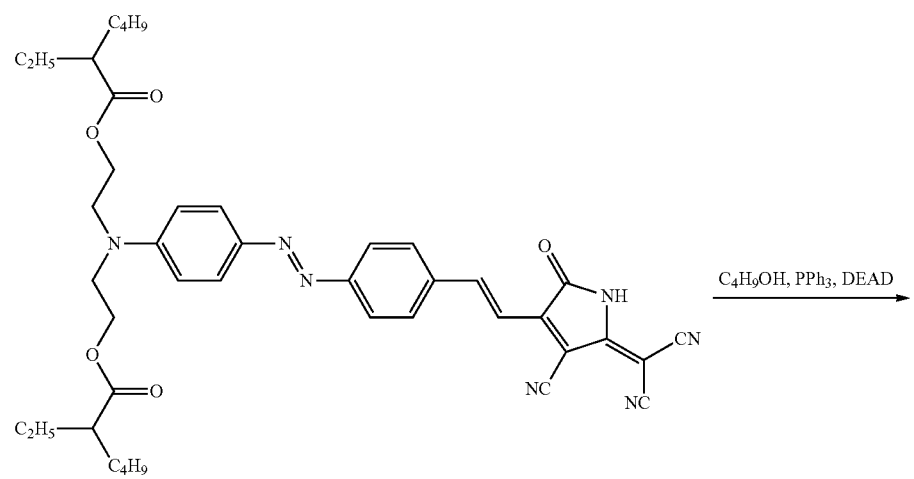

(1)

-continued

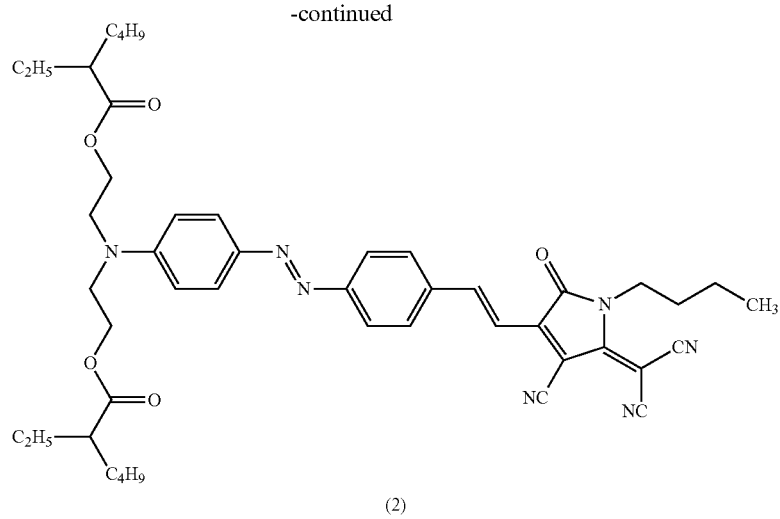

(2)

0.15 g (0.2 mmol) of Exemplary Compound (1), 0.092 g (0.35 mmol) of triphenylphosphine and 0.1 ml (1.1 mmol) of 1-butanol were dissolved in 4 ml of tetrahydrofuran, and 0.17 ml (0.37 mmol) of diethyl azodicarboxylate (2.2 mol/l toluene solution) was added dropwise under nitrogen flow condition and under ice-cooling. The reactants were warmed to room temperature and stirred for 5 hours, and the solvent was distilled off under reduced pressure. The resulting solid was washed with ethanol, and the crystals were separated by filtration. The obtained crystals were purified by silica gel column chromatography (chloroform) to yield Exemplary Compound (2). The quantity was 1.12 g, and the yield was 74%.

$^1$H NMR (CDCl$_3$) δ 8.50 (d, 1H), 7.92 (d, 2H), 7.90 (d, 2H), 7.79 (d, 2H), 7.28 (d, 1H), 6.91 (d, 2H), 4.34 (t, 4H), 4.19 (t, 2H), 3.77 (t, 4H), 2.27 (m, 2H), 1.39-1.78 (m, 12H), 1.15~1.34 (m, 8H), 0.99 (t, 3H), 0.88 (m, 12H) ppm UV-Vis spectrum: $\lambda_{max}$=626 nm (chloroform solution)

Synthesis Example 3

Preparation of Exemplary Compound (51)

Synthesis was performed, it was synthesized in the same manner in the synthesis of Exemplary Compound (1), except that N,N-bis(2-hydroxyethyl)-3-methoxyaniline was used instead of N-phenyethanolamine. N,N-bis(2-hydroxyethyl)-3-methoxyaniline was synthesized with reference to the method described in "Bio-Organic and Medicinal Chemistry Letters (Bioorg. Med. Chem. Lett)", 21, (2011), pp. 940-943.

Synthesis Example 4

Preparation of Exemplary Compound (12)

Exemplary Compound (12) was prepared according to the following scheme. In addition, disodium salt of 4-cyano-5-dicyanomethylidene3-hydroxy-2-oxo-3-pyrroline used as the raw material, for example may be prepared with reference to the method described in U.S. Pat. No. 3,013,013, and N,N-bis-(2-(2-ethylhexanoyloxy)-ethyl)-aniline was synthesized with reference to the procedure described in "Tetrahedron Letters (Tetrahedron. Lett.)", 39, (1998), pp. 6869-6872.

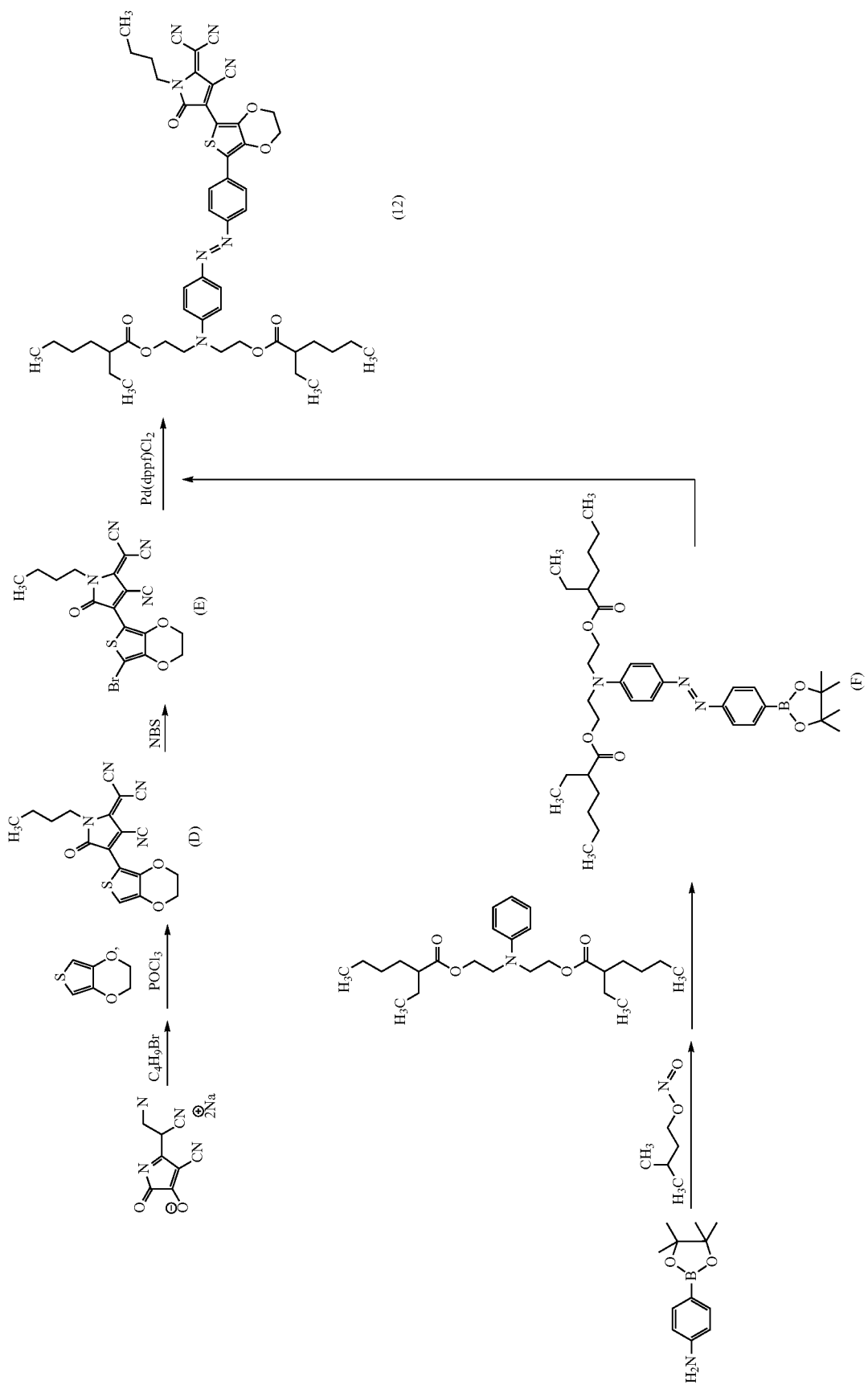

—Synthesis of Intermediate (E)—

4 g (0.017 mol) of disodium salt of 4-cyano-5-dicyanomethylidene3-hydroxy-2-oxo-3-pyrroline and 4.8 g (0.035 mol) of 1-bromobutane were dissolved in 40 ml of N,N-dimethyl formamide, and stirred for 5 hours at 60° C. The reactants were ice-cooled, 5.3 g (0.035 mol) of phosphorus oxychloride was carefully added dropwise not to generate heat in excess stirred for 1 hour, 2.5 g (0.18 mol) of 3,4-ethylenedioxythiophene was added thereto, and the mixture was allowed to warm to room temperature and further stirred for 2 hours. The reaction mixture was added in portions to 400 ml of water to filtrate off the solid, and the resulting solid was purified by silica gel column chromatography (dichloromethane/ethyl acetate=15/1) to give 3.7 g (57% yield) of the intermediate (D). While 80 ml of acetonitrile was added to 3.5 g (0.0096 mol) of the intermediate (D) with stirring at room temperature, and 1.7 g of (0.0096 mol) of N-bromosuccinimide (NBS) was added portionwise. After stirring for 12 hours, the crystals were ice-cooled and separated by filtration to yield 3.8 g (87% yield) of an intermediate (E).

—Synthesis of Intermediate (F)—

50 ml of ethanol and 1.8 ml of concentrated hydrochloric acid were added to 3 g (0.014 mol) of 4-(4,4,5,5-tetramethyl-1,3,2-dioxaborolane)-2-yl)aniline and ice-cooled, and then 2.1 ml (0.016 mol) of isoamyl nitrite was carefully added dropwise thereto with stirring not to generate heat in excess, and stirred further for 1 hour. After 0.18 g (0.002 mol) of the amide sulphate was added to the reaction mixture, 4.8 g (0.011 mol) of N,N-bis-(2-(2-ethylhexanoyloxy)-ethyl)-aniline was added and the mixture was stirred for 3 hours. After warming to room temperature, aqueous solution of sodium hydrogen carbonate was added until neutralization, and 300 ml of ethyl acetate was further added to carry out a liquid separation operation. After the reactants were dehydrated over magnesium sulfate and separated by filtration and the solvent of the organic layer was distilled off under reduced pressure. The obtained solid was purified by silica gel column chromatography (ethyl acetate/n-hexane=1/8) to give 2 g (27% yield) of an intermediate (F).

—Synthesis of Exemplary Compound (12)—

6 ml of 1,2-dimethoxyethane was added to 0.14 g (0.3 mmol) of the intermediate (E), 0.23 g (0.3 mmol) of the intermediate (F), 0.032 g (0.05 mmol) of a (bis(diphenylphosphino)ferrocene) palladium dichloride $CH_2Cl_2$ complex, 0.035 g (0 μmol) of 2-(di-t-butylphosphino)biphenyl and 0.11 g (0.8 mmol) of potassium carbonate, and heated at 85° C. with stirring for 6 hours under nitrogen flow condition. After returning to room temperature, 60 ml of ethyl acetate and 60 ml of water were added, solid was separated by filtration, and the liquid separation operation of the obtained filtrate was carried out. After the reactants were dehydrated over magnesium sulfate and separated by filtration and the solvent of the organic layer was distilled off under reduced pressure. The obtained solid was purified by silica gel column chromatography (dichloromethane/n-hexane=10/1) to give crystals, and the obtained crystals were repeated to wash with ethanol to give Exemplary Compound (12). The quantity was 0.07 g, and the yield was 25%.

$^1$H NMR (CDCl$_3$) δ 8.01 (d, 2H), 7.91 (d, 2H), 7.90 (d, 2H), 6.88 (d, 2H), 4.64 (m, 2H), 4.49 (m, 2H), 4.31 (t, 4H), 4.12 (t, 2H), 3.75 (t, 4H), 2.28 (m, 2H), 1.37-1.78 (m, 12H), 1.18-1.34 (m, 8H), 0.99 (t, 3H), 0.88 (m, 12H) ppm.

UV-Vis spectrum: $\lambda_{max}$=644 nm (chloroform solution)

Synthesis Example 5

Synthesis of Exemplary Compound (94)

Synthesis was performed in the same manner as in the synthesis of Exemplary Compound (12), except that 3,4-dihexylthiophene was used instead of 3,4-ethylenedioxythiophene and 2-(ethyl(meta-toluoyl)amino)-ethyl 2-ethylhexanoate was used instead of N,N-bis-(2-(2-ethylhexanoyloxy)-ethyl)-aniline. 2-(ethyl(meta-toluene) amino)-ethyl 2-ethylhexanoate was synthesized by using N-ethyl-N-2-hydroxyethyl-meta-toluidine and 2-ethylhexanoyl chloride in the same manner as in the synthesis of N,N-bis-(2-(2-ethylhexanoyloxy)-ethyl)-aniline.

Synthesis Example 6

Synthesis of Exemplary Compound (90)

Synthesis was performed by using 2-(ethyl(4-((5-tributylstannyl)thiazol-2-yl)diazenyl)phenyl)amino)ethyl 2-ethylhexanoate instead of the intermediate F in the synthesis of Exemplary Compound (12), and by Stille coupling reaction with the intermediate E. A synthesis of Exemplary compound (90) by preparation of 2-(ethyl(4-((5-tributylstannyl) thiazol-2-yl)diazenyl)phenyl)amino)ethyl 2-ethylhexanoate and Stille coupling reaction was carried out with reference to the procedure described in WO2010/083246A1.

Synthesis Example 7

Synthesis of Exemplary Compound (32)

Exemplary Compound (32) was synthesized according to the following scheme.

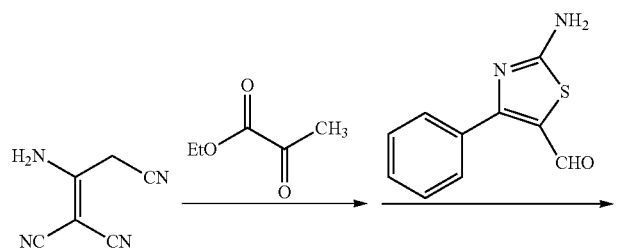

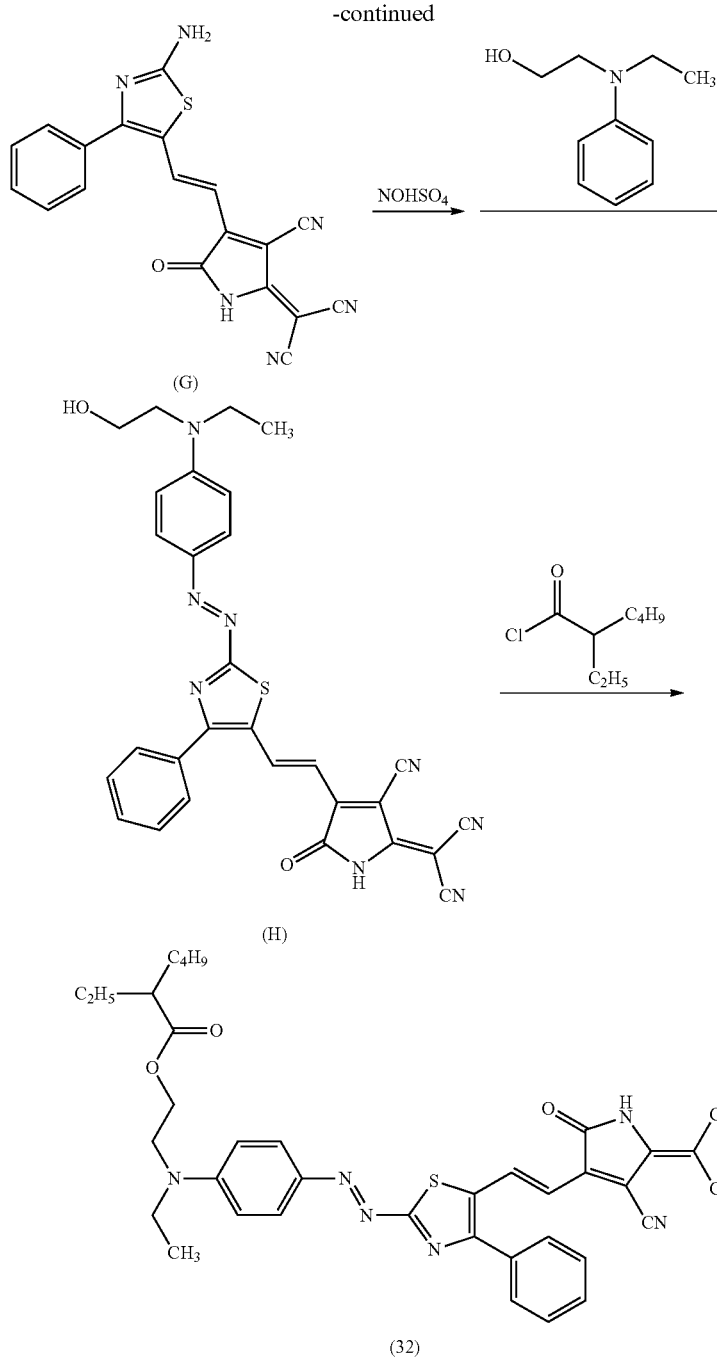

—Synthesis of Intermediate (G)—

2.4 g (0.018 mol) of 2-amino-1,1,3-tricyano-1-propene and 30 ml of ethyl pyruvate 4.2 g (0.036 mol) were added to ethanol, and heated to reflux for 1 hour under nitrogen flow condition. After cooling, 3.0 g (0.015 mol) of 2-amino-4-phenyl-5-formylthiazol was added to the reaction solution, and heated to reflux for 3 hours under nitrogen flow condition. After cooling to room temperature, the precipitated crystals were separated by filtration to give 2.5 g (46% yield) of an intermediate (G).

—Synthesis of Intermediate (H)—

13.5 ml (concentration 85%) of aqueous solution of phosphoric acid was added to 2.5 g (6.7 mmol) of the intermediate (G), and the mixture was stirred under ice-cooling for 30 minutes. 2.6 g (8.2 mmol) of 40% nitrosyl sulfate solution was carefully added thereto dropwise while ice-cooled not to generate heat in excess and stirred further for 1 hour to give a diazonium salt solution of the intermediate (G). The previously prepared diazonium solution was added to the solution of 2.2 g (13.3 mmol) of 2-(N-ethyl-anilino)ethanol dissolved in 120 ml of methanol under being ice-cooled. After being stirred for 2 hours, the crystals were separated by filtration to give 1.9 g (51% yield) of an intermediate (H).

—Synthesis of Exemplary Compound (32)—

0.7 g (1.3 mmol) of an intermediate (H) was dissolved in 25 ml of tetrahydrofuran, heated to 50° C. 0.47 g (5.9 mmol) of pyridine and 0.95 g (5.8 mmol) of 2-ethylhexanoyl chloride was added dropwise thereto, 4-dimethylaminopyridine was added portionwise and heated and stirred at 50° C. for 8 hours. After cooling to room temperature, 150 ml of ethyl acetate was added to the reaction solution to filter off the crystals, and the solvent was distilled off under reduced pressure. The obtained solid was purified by silica gel column chromatography (dichloromethane/ethyl acetate=10/1) to give Exemplary Compound (32). The quantity was 0.46 g, and the yield was 53%.

$^1$H NMR (CDCl$_3$) δ 8.89 (br, 1H), 8.83 (d, 1H), 8.00 (d, 2H), 7.80 (m, 2H), 7.51 (m, 3H), 7.00 (d, 1H), 6.89 (d, 2H), 4.32 (t, 2H), 3.78 (t, 2H), 3.61 (q, 2H), 2.28 (m, 1H), 1.40-1.68 (m, 4H), 1.15-1.37 (m, 7H), 0.86 (m, 6H) ppm.

UV-Vis spectrum: $\lambda_{max}$=748 nm (chloroform solution)

Example 1

Preparation of Organic Nonlinear Optical Material

On the glass substrate provided with ITO layer on the surface (5 cm×5 cm), the solution of 1 part by mass of the Exemplary Compound (1) and 10 parts by weight of Iupilon (R) (Manufactured by Mitsubishi Engineering Plastics Co., Ltd., glass transition temperature: 150° C.) as one kind of polycarbonate dissolved in 89 parts by mass of cyclopentanone (boiling point: 130° C.) was applied by spin coating method, and dried at 120° C. for 1 hour to give a thin film A having a thickness of 1.8 μm. It was visually confirmed that the thin film A was very clear, turbidity or the like did not occur and Exemplary Compound (1) was homogeneously dispersed. In addition, the glass transition temperature of the thin film A was 140° C.

Exemplary Compound (1):

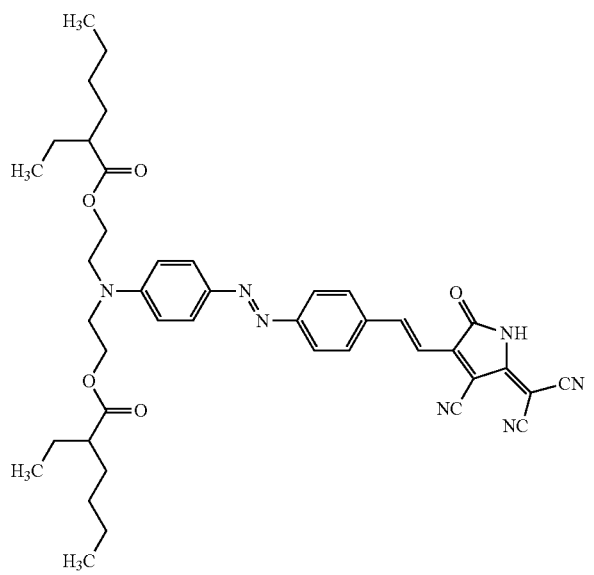 [SMILES: CCCCC(CC)C(=O)OCCN(CCOC(=O)C(CC)CCCC)c1ccc(/N=N/c2ccc(/C=C/C3=C(C#N)C(=C(C#N)C#N)NC3=O)cc2)cc1]

Example 2

Preparation of an organic nonlinear optical material and its evaluation were carried out in the same manner as the above except for using the following Exemplary Compound (8) instead of Exemplary Compound (1) of Example 1. It was visually confirmed that the film was very clear, turbidity or the like did not occur and Exemplary Compound (8) was homogeneously dispersed.

Exemplary Compound (8):

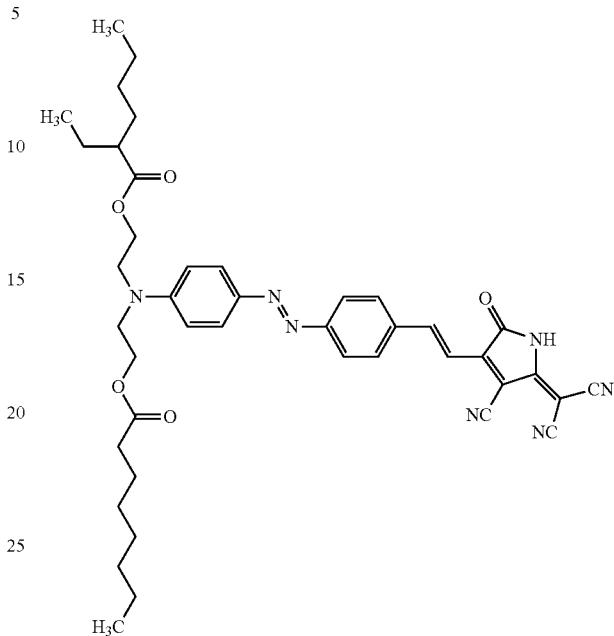

Example 3

Preparation of an organic nonlinear optical material and its evaluation were carried out in the same manner as the above except for using the following Exemplary Compound (2) instead of Exemplary Compound (1) of Example 1. It was visually confirmed that the film was very clear, turbidity or the like did not occur and Exemplary Compound (2) was homogeneously dispersed.

Exemplary Compound (2):

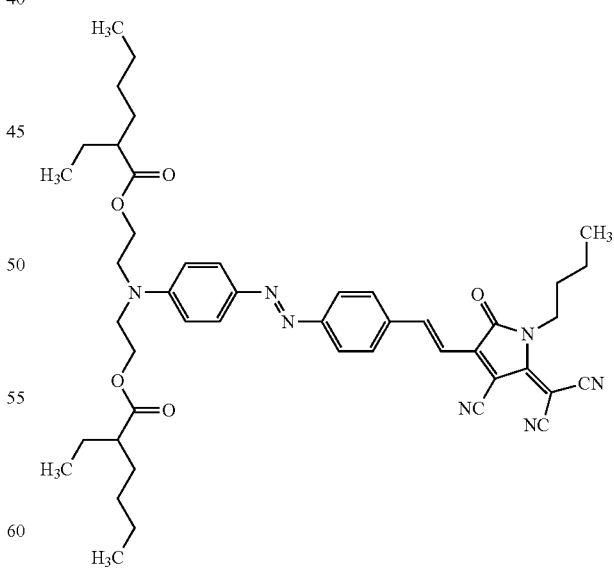

Example 4

Preparation of an organic nonlinear optical material and its evaluation were carried out in the same manner as the above except for using the following Exemplary Compound (12) instead of Exemplary Compound (1) of Example 1. It was visually confirmed that the film was very clear, turbidity or the like did not occur and Exemplary Compound (12) was homogeneously dispersed.

Exemplary Compound (12):

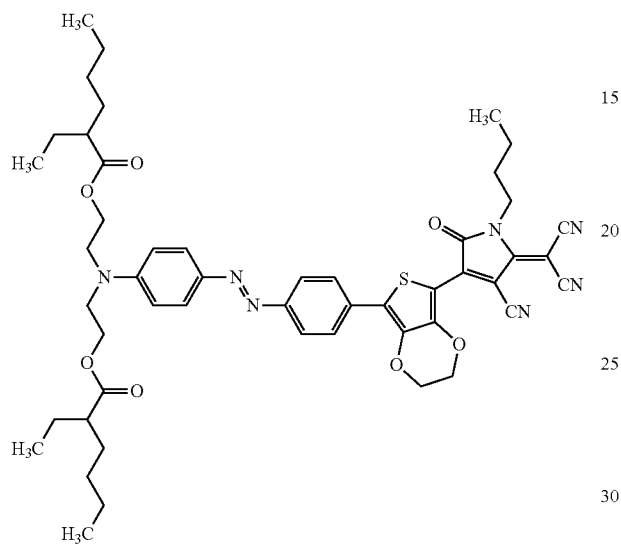

Exemplary compound (51):

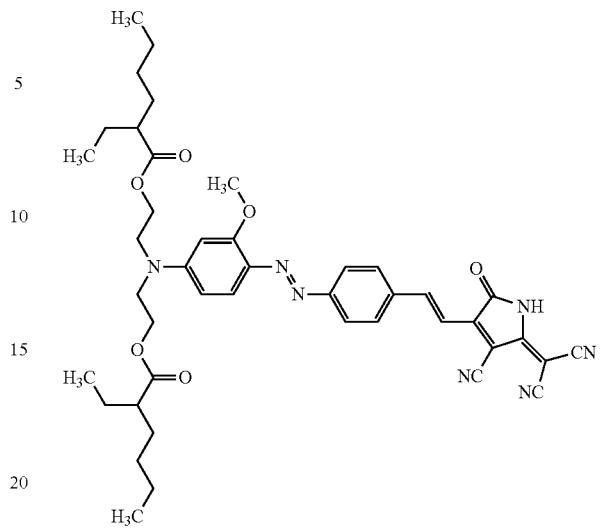

Example 6

Preparation of an organic nonlinear optical material and its evaluation were carried out in the same manner as the above except for using the following Exemplary Compound (94) instead of Exemplary Compound (1) of Example 1. It was visually confirmed that the film was very clear, turbidity or the like did not occur and Exemplary Compound (94) was homogeneously dispersed.

Exemplary compound (94):

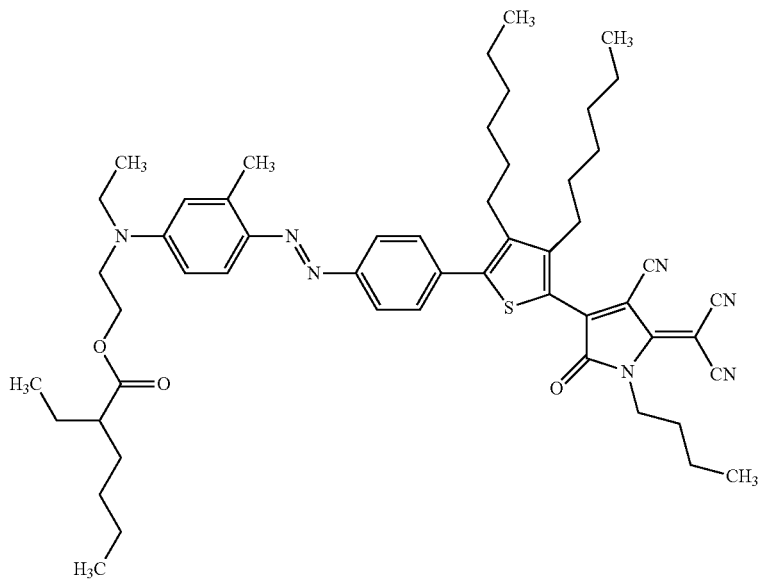 [SMILES: CCCCCCc1c(C2=C(C#N)C(=C(C#N)C#N)N(CCCC)C2=O)sc(-c2ccc(/N=N/c3ccc(N(CC)CCOC(=O)C(CC)CCCC)cc3C)cc2)c1CCCCCC]

Example 5

Preparation of an organic nonlinear optical material and its evaluation were carried out in the same manner as the above except for using the following Exemplary Compound (51) instead of Exemplary Compound (1) of Example 1. It was visually confirmed that the film was very clear, turbidity or the like did not occur and Exemplary Compound (51) was homogeneously dispersed.

Example 7

Preparation of an organic nonlinear optical material and its evaluation were carried out in the same manner as the above except for using the following Exemplary Compound (90) instead of Exemplary Compound (1) of Example 1. It was visually confirmed that the film was very clear, turbidity or the like did not occur and Exemplary Compound (90) was homogeneously dispersed.

Exemplary compound (90):

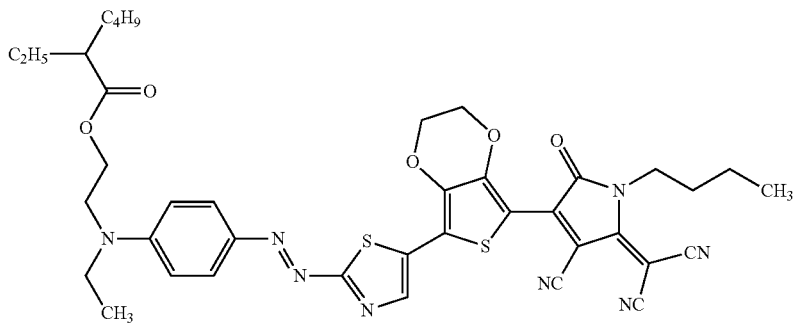

Example 8

Preparation of an organic nonlinear optical material and its evaluation were carried out in the same manner as the above except for using the following Exemplary Compound (32) instead of Exemplary Compound (1) of Example 1. It was visually confirmed that the film was very clear, turbidity or the like did not occur and Exemplary Compound (32) was homogeneously dispersed.

Exemplary compound (32):

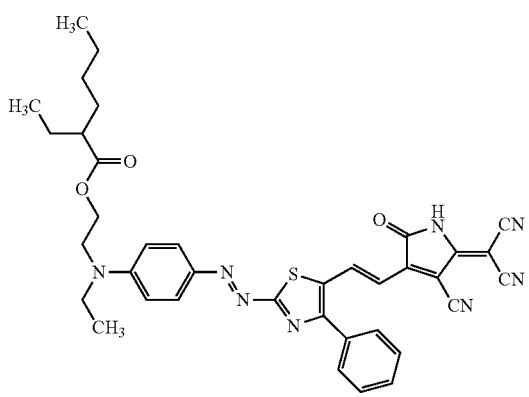 [SMILES: CCCCC(CC)C(=O)OCCN(CC)c1ccc(/N=N/c2nc(-c3ccccc3)c(/C=C/C3=C(C#N)C(=C(C#N)C#N)NC3=O)s2)cc1]

Example 9

Preparation of an organic nonlinear optical material and its evaluation were carried out in the same manner as the above except for using the following Exemplary Compound (27) instead of Exemplary Compound (1) of Example 1. It was visually confirmed that the film was very clear, turbidity or the like did not occur and Exemplary Compound (27) was homogeneously dispersed.

Exemplary Compound (27):

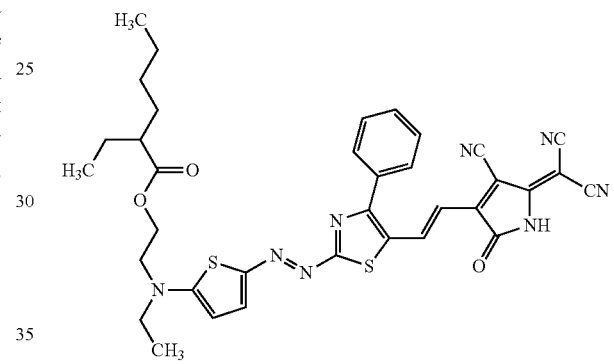

Example 10

On the glass substrate provided with ITO layer on the surface (5 cm×5 cm), the solution of 1 part by mass of the Exemplary Compound (32) and 10 parts by weight of polymethyl methacrylate (Manufactured by Alfa Aesar Inc., molecular weight: 125,000) as one kind of polycarbonate dissolved in 89 parts by weight of cyclopentanone (boiling point: 130° C.) was applied by spin coating method, and dried at 120° C. for 1 hour to give a thin film A' having a thickness of 1.8 μm. The glass transition temperature of the film A' was 110° C. In addition, as for the thin film A' obtained according to the present invention, the holding temperature was kept to 110° C. in the evaluation of the stability during the processing poling electric field (polarization) and alignment stability, and the processing poling electric field (polarization) was conducted to give a thin film C.

Comparative Example 1

Preparation of an organic nonlinear optical material and its evaluation were carried out in the same manner, except that the following Exemplary Compound (X) (Dispers Red1: Manufactured by Aldrich Co.) was used instead of Exemplary Compound (1) of Example 1.

Exemplary Compound (X):

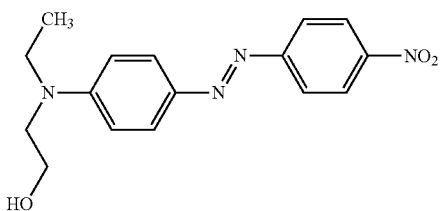 [SMILES: CCN(CCO)c1ccc(/N=N/c2ccc([N+](=O)[O-])cc2)cc1]

Comparative Example 2

Preparation of an organic nonlinear optical material and its evaluation were carried out in the same manner, except that the following Exemplary Compound (Y) was used instead of Exemplary Compound (1) of Example 1.
Exemplary compound (Y):

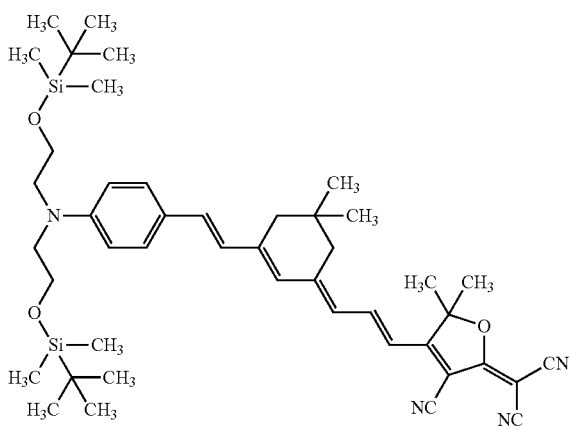 [SMILES: CC1(C)CC(/C=C/c2ccc(N(CCO[Si](C)(C)C(C)(C)C)CCO[Si](C)(C)C(C)(C)C)cc2)=CC(=C/C=C/C2=C(C#N)C(=C(C#N)C#N)OC2(C)C)/C1]

Comparative Example 3

Preparation of an organic nonlinear optical material and its evaluation were carried out in the same manner, except that the following Exemplary Compound (Z) was used instead of Exemplary Compound (1) of Example 1.
Exemplary Compound (Z):

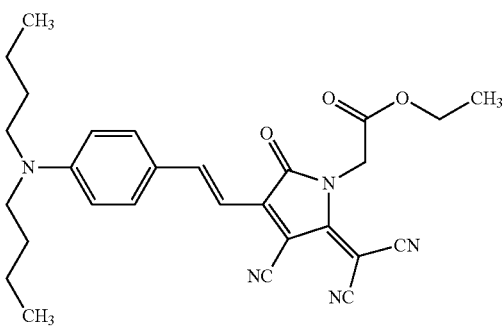 [SMILES: CCCCN(CCCC)c1ccc(/C=C/C2=C(C#N)C(=C(C#N)C#N)N(CC(=O)OCC)C2=O)cc1]

Comparative Example 4

Preparation of an organic nonlinear optical material and its evaluation were carried out in the same manner, except that the following Exemplary Compound (Z) was used instead of Exemplary Compound (32) of Example 10.

Comparative Example 5

Preparation of an organic nonlinear optical material and its evaluation were carried out in the same manner, except that the following Exemplary Compound (X) was used instead of Exemplary Compound (Z) of Comparative Example 4.

The above evaluation results are shown in Table 1.

(Evaluation)

—Heat Resistance—

The obtained thin film A was placed on a hot plate, held at 140° C. which is the poling process temperature for 15 minutes under an air atmosphere below white light, and held at 230° C. for 1 minute as a temperature indicator when mounting solder such as a printed circuit board. After that, deterioration of Exemplary Compound (1) before and after heating was measured by visible infrared polarization spectrophotometer (Manufactured by Nippon Bunko Inc. V-670ST).

Further, the deterioration rate in the heat resistance evaluation of the organic compound having a nonlinear optical activity was listed in Table 1 as the deterioration rate by measuring the absorption spectrum in the visible region of (a) the thin film A in which the nonlinear optically active compound obtained in the above order was randomly oriented, and (b) the thin film B in which the thin film A was placed on a hot plate, and held at 140° C. for 15 minutes or at 230° C. for 1 minute under an air atmosphere below white light with a photometer, and by calculating the deterioration rate of the organic compound having a nonlinear optical activity by thermal aging in the following equation (1) from the wavelength λmax which absorption is maximized.

Further, in heat resistance evaluation, the deterioration rate when the film was held at 140° C. for 15 minutes was evaluated in four stages, A for from 0.00 to 0.01, B for from 0.01 to 0.02, C for from 0.02 to 0.03, and D for 0.03 or more.

Moreover, the deterioration rate when the film was held at 230° C. for 1 minute was evaluated in four stages, A for from 0.00 to 0.01, B for from 0.01 to 0.05, C for from 0.05 to 0.10, and D for 0.10 or more. In addition, in practice, it is preferred that it is not D.

$$\delta = 1 - A_t / A_0 \qquad \text{Equation (1)}$$

(However, in Equation (1), δ represents the deterioration rate of the organic compound having nonlinear optical activity, $A_t$ represents the absorbance at the wavelength λmax of the thin film B, and $A_0$ represents the absorbance at the wavelength λmax of the thin film A.)

—Light Resistance—

Further, laser light (25 mW) of 1312 nm, which is one of the communication wavelength, was irradiated to the obtained film A for 3 hours under an air atmosphere by Prism Coupler (Model2010, Manufactured by Metricon Co., Ltd.). The deterioration in the thin film of Exemplary Compound (1) before and after irradiation was measured by the change in refractive index by the prism coupler. In addition, it was determined that when the refractive index was changed, there was deterioration of the organic compound having a nonlinear optical activity. The higher the amount of change was, the higher the degree of deterioration was determined. The change amount of the refractive index was evaluated in four stages, A for from 0.00 to $1.00 \times 10^{-4}$, B for from $1.00×10^{-4}$ to $3.00×10^{-4}$, C for from $3.00×10^{-4}$ to $5.00×10^{-4}$, and D for $5.00×10^{-4}$ or more. In addition, in practice, it is preferred that it is not D.

—Stability when Processing Electric Field Poling (Polarization)—

Further, the obtained thin film A was placed on a hot plate, and the film A was subjected to treatment by corona poling. Specifically, while a charging voltage of 17 kV was applying at intervals of 30 mm from the film A, the film A was held at 140° C. for 0.5 minutes, and then, while the charging voltage from the state was applying, the film A was cooled over 10 minutes to 40° C. which is below the glass transition temperature of the film A in order to remove the charging voltage. The deterioration of the organic compound having a nonlinear optical activity when poling the film A was measured by the above mentioned visible infrared polarization spectrophotometer.

Further, the deterioration rate in the stability evaluation when processing polarizing the organic compound having a nonlinear optical activity was listed in Table 1 as the deterioration rate by measuring the absorption spectrum in the visible region of the thin film A and the thin film D in the following:

the thin film A in which the nonlinear optically active compound obtained in the above order was randomly oriented, (2) the thin film C in which the thin film A was placed on a hot plate, and while a charging voltage of 17 kV was applying at intervals of 30 mm from the film A, the film A was held at 140° C. for 0.5 minutes, and then, while the charging voltage from the state was applying, the film A was cooled over 10 minutes to 40° C. which is below the glass transition temperature of the film A in order to remove the charging voltage, (3) the thin film D in which the thin film C was held for 10 minutes without applying a charging voltage at a temperature which had been subjected to corona poling process, and allowed to orientation relaxation, with a photometer, and by calculating the deterioration rate from the following equation (2).

$$\delta = 1 - A_t / A_0 \qquad \text{Equation (2)}$$

(However, in Equation (2), $\delta$ represents the deterioration rate of the organic compound having a nonlinear optical activity, $A_t$ represents the absorbance at the wavelength $\lambda$max of the thin film D, and $A_0$ represents the absorbance at the wavelength $\lambda$max of the thin film A.)

In addition, the deterioration rate in the stability evaluation when processing polarization was evaluated in four stages, A for from 0.00 to 0.03, B for from 0.03 to 0.06, C for from 0.06 to 0.10, and D for 0.10 or more. Further, in practice, it is preferred that it is not D.

—Orientation Efficiency—

In addition, the order parameter was obtained as an indicator of the orientation efficiency due to the electric field poling treatment.

The above order parameter was calculated by measuring the absorption spectrum in the visible region of (4) the thin film C in which the film A was subjected to the corona poling process, and the nonlinear optically active compound was oriented in the thickness direction, (5) the thin film D in which the film C was held for 10 minutes without applying a charging voltage at a temperature which had been subjected to corona poling process, and allowed to orientation relaxation, with a photometer, and by calculating the order parameter from the following equation (3).

$$\phi = 1 - B_t / A_1 \qquad \text{Equation (3)}$$

(However, in Equation (3), $\phi$ represents the order parameter, $B_t$ represents the absorbance at the wavelength $\lambda$max of the thin film C of the poling process, and $A_1$ represents the absorbance at the wavelength $\lambda$max of the thin film D.)

In addition, the order parameter in the orientation efficiency evaluation was evaluated in four stages, A for 0.20 or more, B for from 0.10 to 0.20, C for from 0.08 to 0.10, and D for less than 0.08. Further, in practice, it is preferred that it is not D.

—Nonlinear Optical Performance—

Further, for Exemplary Compounds of the Examples and the Comparative Examples, the hyperpolarization ratio $\beta_0$ was calculated as an index of the nonlinear optical performance by the quantum chemical calculation program (SCIGRESS, Manufactured by Fujitsu) using the AM1 method. $\beta_0$ value was also shown in Table 1.

In addition, $\beta_0$ value in the nonlinear optical performance evaluation was evaluated in four stages, A for 200 or more, B for from 150 to 200, C for from 100 to 150, and D for less than 100. Further, in practice, it is preferred that it is not D.

TABLE 1

|  | Heat Resistance | | Light Resistance | Stability during | Orientation | Nonlinear Optical | |
| --- | --- | --- | --- | --- | --- | --- | --- |
|  | Deterioration Rate δ 140° C.(15 min) | Deterioration Rate δ 230° C.(1 min) | Change Amount of Refractive Index (×10⁻⁴) | Processing Polarizing Deterioration Rate δ | Efficiency Order Parameter φ | Performance Calculation β₀ (10⁻³⁰ esu) | Comprehensive Evaluation |
| Example 1 | 0.01 | 0.04 | 1.0 | 0.05 | 0.10 | 210 | B |
| (Exemplary compound 1) | B | B | B | B | B | A | |
| Example 2 | 0.01 | 0.04 | 1.0 | 0.05 | 0.10 | 210 | B |
| (Exemplary compound 8) | B | B | B | B | B | A | |
| Example 3 | 0.01 | 0.06 | 3.0 | 0.05 | 0.10 | 210 | B |
| (Exemplary compound 2) | B | C | C | B | B | A | |
| Example 4 | 0.00 | 0.00 | 0.0 | 0.02 | 0.20 | 170 | A |
| (Exemplary compound 12) | A | A | A | A | A | B | |
| Example 5 | 0.01 | 0.05 | 1.0 | 0.05 | 0.12 | 210 | B |
| (Exemplary compound 51) | B | C | B | B | B | A | |
| Example 6 | 0.00 | 0.00 | 1.0 | 0.02 | 0.21 | 140 | B |
| (Exemplary compound 94) | A | A | B | A | A | C | |
| Example 7 | 0.01 | 0.04 | 1.0 | 0.02 | 0.16 | 190 | B |
| (Exemplary compound 90) | B | B | B | A | B | B | |

TABLE 1-continued

| | Heat Resistance | | Light Resistance | Stability during | Orientation | Nonlinear Optical | |
|---|---|---|---|---|---|---|---|
| | Deterioration Rate δ 140° C.(15 min) | Deterioration Rate δ 230° C.(1 min) | Change Amount of Refractive Index (×10$^{-4}$) | Processing Polarizing Deterioration Rate δ | Efficiency Order Parameter φ | Performance Calculation β$_0$ (10$^{-30}$ esu) | Comprehensive Evaluation |
| Example 8 | 0.01 | 0.09 | 3.0 | 0.03 | 0.08 | 270 | C |
| (Exemplary compound 32) | B | C | C | B | C | A | |
| Example 9 | 0.02 | 0.09 | 3.0 | 0.05 | 0.10 | 330 | C |
| (Exemplary compound 27) | C | C | C | B | B | A | |
| Comparative Example 1 | 0.01 | 0.50 | 0.3 | 0.05 | 0.20 | 60 | D |
| (Exemplary compound X) | B | D | A | B | A | D | |
| Comparative Example 2 | 0.03 | 0.10 | 5.5 | 0.12 | 0.05 | 370 | D |
| (Exemplary compound Y) | D | D | D | D | D | A | |
| Comparative Example 3 | 0.01 | 0.30 | 3.0 | 0.06 | 0.10 | 160 | D |
| (Exemplary compound Z) | B | D | C | C | B | B | |

A comprehensive evaluation was conducted from the evaluation results of each item. From the viewpoint of practical use, the evaluation value of each item is preferably A, B or C, and more preferably A or B. Thus, as a comprehensive evaluation, if two or more items of A exist and any items of C and D do not exist, it is set for "A", if one or more items of A exist, items less than two of C exist and any items of D do not exist, it is set for "B", if one or more items of A exist, three or more items of C exist and any items of D do not exist, it is set for "C", and if any one item of D exists, it is set for "D".

From the above results, it may be seen that the organic compound having a nonlinear optical activity used for the nonlinear optical material of the present invention had a high nonlinear optical performance. Further, the nonlinear optical material of the present invention was found to be excellent in heat resistance, light resistance, and moreover its stability was excellent even though the electric field poling was conducted.

—Orientation Stability—

In addition, the retention ratio (τ) of the orientation was calculated by measuring the order parameter of the thin film immediately after corona poling processing and after standing at 45° C. for 3 hours as an index of the stability of organic orientation induced by the in the following procedure:

(6) The order parameter was calculated by corona poling processing the thin film A and the thin film A', and orienting the nonlinear optically active compound in the thickness direction to give the thin film C and the thin film C' by the above equation (3).

(7) The order parameter was calculated by standing the thin film C and the thin film C' at 45° C. for 3 hours to give the thin film E and the thin film E' by the above equation (3).

(8) The retention ratio (τ) of the order parameter was calculated by the following equation (4).

$$\tau = \phi_{3h} / \phi_{0h} \times 100 \qquad \text{Equation (4)}$$

(However, in Equation (4), τ represents the retention ratio of the orientation, $\phi_{0h}$ represents the order parameter immediately after the corona poling, and $\phi_{3H}$ represents the order parameter after standing at 45° C. for 3 hours from immediately after the corona poling.)

In addition, the retention ratio of the orientation in the orientation stability evaluation was evaluated in four stages, A for 90% or more, B for from 80% to 90%, C for from 70% to 80%, and D for less than 70%. Further, in practice, it is preferred that it is not D.

The evaluation results of the orientation stability were shown in Table 2.

TABLE 2

| | Polymer Binder | Glass Transition Temperature (° C.) | Retention Rate of Orientation τ (%) | Evaluation |
|---|---|---|---|---|
| Example 1 (Exemplary compound 1) | Polycarbonate | 140 | 90 | A |
| Example 8 (Exemplary compound 32) | Polycarbonate | 140 | 92 | A |
| Example 10 (Exemplary compound 32) | Polymethyl methacrylate | 110 | 82 | B |
| Comparative Example 1 (Exemplary compound X) | Polycarbonate | 140 | 72 | C |
| Comparative Example 4 (Exemplary compound Z) | Polymethyl methacrylate | 110 | 79 | C |
| Comparative Example 5 (Exemplary compound X) | Polymethyl methacrylate | 110 | 45 | D |

It has been found that, from the above results, the organic nonlinear materials having an excellent orientation stability after the electric field poling was obtained by combining the exemplary compounds of the present invention and a polymeric binder such as polycarbonate having a high glass transition temperature.

INDUSTRIAL APPLICABILITY

According to the present invention, there is provided an organic nonlinear optical material containing a polymer binder and an organic compound having an excellent specific nonlinear optical activity such as excellent nonlinear optical performance, light resistance, sublimation resistance and voltage resistance. Thus, a polymeric binder having high stability about heat or voltage in the process to achieve the orientation state and high stability about light (for example, wavelength of 1.3 μm), high nonlinear optical activity in the actual drive and high glass transition temperature may be applied. Therefore, the present invention represents desirable effects such may keeping orientation state of the organic compound having a nonlinear optical activity for a long period of time.

It is possible to realize a nonlinear optical device excellent in the stability and other several properties by using an organic nonlinear optical material of the present invention.

The present invention was described with reference to specific embodiments in detail, but it is evident to those skilled in the art that various changes and modifications without departing from the spirit and scope of the present invention will be apparent.

The present application is based on Japanese patent application (No. 2012-078096) filed on Mar. 29, 2012, and the contents of which are incorporated herein by reference.

What is claimed is:

1. A compound represented by the following Formula (II):

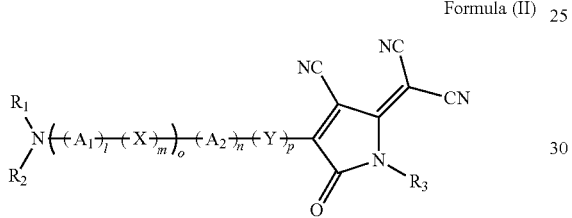

Formula (II)

wherein, in Formula (II), $R_1$ and $R_2$ each independently represent a substituted or unsubstituted alkyl group or a substituted or unsubstituted aryl group;

$R_3$ represents a hydrogen atom, a substituted or unsubstituted alkyl group, or a substituted or unsubstituted aryl group;

$A_1$ and $A_2$ each independently represent a substituted or unsubstituted aromatic group;

X represents —$CR_4$=$CR_5$—, —C≡C—, —$CR_6$=N—, —N=$CR_7$— or —N=N—;

Y represents —$CR_8$=$CR_9$— or a substituted or unsubstituted aromatic group;

$R_4$, $R_5$, $R_6$, $R_7$, $R_8$ and $R_9$ each independently represent a hydrogen atom, a substituted or unsubstituted alkyl group, or a substituted or unsubstituted aryl group;

l and n each independently represent an integer of 0 to 3;

m, o, and p each independently represent an integer of 1 to 3;

each of $R_4$'s, $R_5$'s, $R_6$'s, $R_7$'s, $R_8$'s, $R_9$'s, $A_1$'s, $A_2$'s, X's, Y's, l's and m's may be the same or different, and at least one of X's contains —N=N—.

* * * * *